(12) United States Patent
Dyhrfjeld-Johnsen

(10) Patent No.: US 11,612,605 B2
(45) Date of Patent: *Mar. 28, 2023

(54) (+)-AZASETRON FOR USE IN THE TREATMENT OF EAR DISORDERS

(71) Applicant: SENSORION, Montpellier (FR)

(72) Inventor: Jonas Dyhrfjeld-Johnsen, Lunel-Viel (FR)

(73) Assignee: SENSORION, Montpellier (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/093,911

(22) PCT Filed: Apr. 14, 2017

(86) PCT No.: PCT/EP2017/059058
§ 371 (c)(1),
(2) Date: Oct. 15, 2018

(87) PCT Pub. No.: WO2017/178645
PCT Pub. Date: Oct. 19, 2017

(65) Prior Publication Data
US 2019/0083503 A1    Mar. 21, 2019

Related U.S. Application Data

(60) Provisional application No. 62/322,690, filed on Apr. 14, 2016.

(30) Foreign Application Priority Data

Jul. 19, 2016   (EP) .................................... 16180192

(51) Int. Cl.
*A61K 31/538*    (2006.01)
*A61P 27/16*    (2006.01)
*A61K 9/00*    (2006.01)

(52) U.S. Cl.
CPC ............ *A61K 31/538* (2013.01); *A61P 27/16* (2018.01); *A61K 9/0056* (2013.01)

(58) Field of Classification Search
None
See application file for complete search history.

(56) References Cited

U.S. PATENT DOCUMENTS

| | | | |
|---|---|---|---|
| 4,695,578 A | 9/1987 | Coates et al. | |
| 4,892,872 A | 1/1990 | Tahara et al. | |
| 5,360,800 A | 11/1994 | Coates et al. | |
| 6,063,802 A | 5/2000 | Winterborn | |
| 6,758,840 B2 | 7/2004 | Knox | |
| 8,580,730 B2 | 11/2013 | Chabbert et al. | |
| 2003/0229333 A1* | 12/2003 | Ashton ................ | A61K 9/0046 604/514 |
| 2004/0147510 A1 | 7/2004 | Landau et al. | |
| 2004/0204466 A1 | 10/2004 | Agarwal et al. | |
| 2004/0241159 A1 | 12/2004 | De Cellery D'Allens | |
| 2006/0074101 A1 | 4/2006 | Baroni et al. | |
| 2007/0160648 A1 | 7/2007 | Ashton et al. | |
| 2007/0265329 A1 | 11/2007 | Devang et al. | |
| 2010/0266607 A1 | 10/2010 | Fox | |
| 2015/0038594 A1* | 2/2015 | Borges ................ | A61K 9/0056 514/772.2 |
| 2015/0174148 A1 | 6/2015 | Brown et al. | |
| 2018/0207167 A1 | 7/2018 | Dyhrfjeld-Johnsen | |

FOREIGN PATENT DOCUMENTS

| | | |
|---|---|---|
| CN | 101786963 A | 7/2010 |
| CN | 104557906 A | 4/2015 |
| EP | 1 250 925 A2 | 10/2002 |
| EP | 2 253 316 A1 | 11/2010 |
| JP | 2011-528036 A | 11/2011 |
| JP | 2015-524408 A | 8/2015 |
| WO | 02/067987 A2 | 9/2002 |
| WO | 03/071986 A2 | 9/2003 |
| WO | 03/105832 A1 | 12/2003 |
| WO | 2010/008995 A2 | 1/2010 |
| WO | 2010/133663 A1 | 11/2010 |
| WO | 2013/124416 A1 | 8/2013 |
| WO | 2016/184900 A1 | 11/2016 |

OTHER PUBLICATIONS

Agranat et al. "Putting Chirality to Work: The Strategy of Chiral Switches". Nat Rev Drug Discov. Oct. 2002; 1(10):753-768. (Year: 2002).*
Rauch SD. "Idiopathic Sudden Sensorineural Hearing Loss". N Engl J Med. 2008; 359:833-840. (Year: 2008).*
Petremann et al. "Oral Administration of Clinical Stage Drug Candidate SENS-401 Effectively Reduces Cisplatin-Induced Hearing Loss in Rats". Otol Neurotol. Oct. 2017; 38(9):1355-1361. [Abstract Only] (Year: 2017).*
CAS Registry No. 123040-16-4. "Azasetron Hydrochloride". Retrieved from CAS Registry [Sep. 24, 2021]. pp. 1-2. (Year: 2021).*
Kuhn et al. "Sudden Sensorineural Hearing Loss: A Review of Diagnosis, Treatment, and Prognosis." Trends in Amplification. 2011; 15(3):91-105. (Year: 2011).*
Petremann et al. "Oral Administration of Clinical Stage Drug Candidate SENS-401 Effectively Reduces Cisplatin-Induced Hearing Loss in Rats". Otology & Neurotology. Oct. 2017; 38(9):1355-1361. (Year: 2017).*
Petremann et al. "SENS-401 Effectively Reduces Severe Acoustic Trauma-Induced Hearing Loss in Male Rats with Twice Daily Administration Delayed up to 96 Hours". Otology & Neurotology. Feb. 2019; 40(2):254-263. (Year: 2019).*
Dyhrfjeld-Johnsen et al. "Absorption, Distribution, Metabolism, and Excretion (ADME) Supports SENS-401 as Orally Active Otoprotectant". Otolaryngology—Head and Neck Surgery. Aug. 30, 2017; 157(1; Suppl.). p. P234. (Year: 2017).*
Taslimi et al. "Ondansetron in Patients with Tinnitus: Randomized Double-Blind Placebo-Controlled Study". Eur Arch Otorhinolaryngol. 2013; 270:1635-1641. (Year: 2013).*
Goycoolea et al., "Round window membrane. Structure function and permeability: a review." Microscopy Research and Technique Feb. 1, 1997;36(3):201-11.
Sergi et al., "Cisplatin ototoxicity in the guinea pig: vestibular and cochlear damage" Hearing Research, Aug. 2003;182(1-2):56-64.

(Continued)

*Primary Examiner* — Leslie A. Royds Draper
(74) *Attorney, Agent, or Firm* — Nixon & Vanderhye

(57) ABSTRACT

Disclosed is a method for treating ear disorders, including the administration of (+)-azasetron, or a pharmaceutically acceptable salt and/or solvate thereof.

20 Claims, 8 Drawing Sheets

(56) References Cited

OTHER PUBLICATIONS

Binks et al., "PneuMum: Impact from a randomised controlled trial of maternal 23-valent pneumococcal polysaccharide vaccination on middle ear disease amongst Indigenous infants, Northern Territory, Australia." Vaccine, Nov. 27, 2015;33(48):6579-87.
Vambutas et al., "Early efficacy trial of anakinra in corticosteroid-resistant autoimmune inner ear disease." Journal of Clinical Investigation, Sep. 2014;124(9):4115-22.
Bas et al., "An experimental comparative study of dexamethasone, melatonin and tacrolimus in noise-induced hearing loss". Acta Otolaryngol. Apr. 2009;129(4):385-9.
Crane et al., "Steroids for treatment of sudden sensorineural hearing loss: a meta-analysis of randomized controlled trials". Laryngoscope. Jan. 2015;125(1):209-17.
Di Leo et al., "Late recovery with cyclosporine-A of an autoimmune sudden sensorineural hearing loss". Acta Otorhinolaryngol Ital. Dec. 2011;31(6):399-401.
Filipo et al., "Oral versus short-term intratympanic prednisolone therapy for idiopathic sudden hearing loss". Audiol Neurootol. 2014;19(4):225-33.
Kramer et al., "Calcineurin controls the expression of numerous genes in cerebellar granule cells". Mol Cell Neurosci. Jun. 2003;23(2):325-30.
Lin et al., "Hearing loss and cognitive decline in older adults". JAMA Intern Med. Feb. 25, 2013;173(4):293-9.
McClelland et al., "Role of ciclosporin in steroid-responsive sudden sensorineural hearing loss". Acta Otolaryngol. Dec. 2005;125(12):1356-60.
Naesens & Sarwal, "Monitoring calcineurin inhibitor therapy: localizing the moving target". Transplantation. Jun. 15, 2010;89(11):1308-9.
Naesens et al., "Calcineurin inhibitor nephrotoxicity". Clin J Am Soc Nephrol. Feb. 2009;4(2):481-508.
Shupak et al., "Otoacoustic emissions in the prediction of sudden sensorineural hearing loss outcome". Otol Neurotol. Dec. 2014;35(10):1691-7.
Uemaetomari et al., "Protective effect of calcineurin inhibitors on acoustic injury of the cochlea". Hear Res. Nov. 2005;209(1-2):86-90.
Vallano et al., "Depolarization and Ca(2+) down regulate CB1 receptors and CB1-mediated signaling in cerebellar granule neurons". Neuropharmacology. May 2006;50(6):651-60.
Viberg & Canlon, "The guide to plotting a cochleogram". Hear Res. Nov. 2004;197(1-2):1-10.
Yamashita et al., "Delayed production of free radicals following noise exposure". Brain Res. Sep. 3, 2004;1019(1-2):201-9.
Yang et al., "Quantitative analysis of apoptotic and necrotic outer hair cells after exposure to different levels of continuous noise". Hear Res. Oct. 2004;196(1-2):69-76.
Dyhrfjeld-Johnsen et al., "Ondansetron reduces lasting vestibular deficits in a model of severe peripheral excitotoxic injury". J Vestib Res. 2013;23(3):177-86.
Venail et al., "A protective effect of 5-HT3 antagonist against vestibular deficit? Metoclopramide versus ondansetron at the early stage of vestibular neuritis: a pilot study." Eur Ann Otorhinolaryngol Head Neck Dis. Apr. 2012;129(2):65-8.
Jackson & Silverstein, "Meniere's Disease: Diagnosis, Natural History, and Current Management." Aug. 19, 2002 https://www.audiologyonline.com/articles/meniere-s-disease-diagnosis-natural-1161.
Jellish et al., "Ondansetron versus droperidol or placebo when given prophylactically for the prevention of postoperative nausea and vomiting in patients undergoing middle ear procedures". J Clin Anesth. Sep. 1997;9(6):451-6.
Rice & Ebers, "Ondansetron for intractable vertigo complicating acute brainstem disorders." Lancet. May 6, 1995;345(8958):1182-3.
Mandelcorn et al., "A preliminary study of the efficacy of ondansetron in the treatment of ataxia, poor balance and incoordination from brain injury." Brain Inj. Oct. 2004;18(10):1025-39.
Hain et al., "Pharmacologic treatment of persons with dizziness." Neurol Clin. Aug. 2005;23(3):831-53.
Tsukagoshi et al., "Pharmacokinetics of azasetron (Serotone), a selective 5-HT3 receptor antagonist" Gan To Kagaku Ryoho. Jun. 1999;26(7):1001-8 (abstract only).
Smith et al., "Zacopride, a potent 5-HT3 antagonist." J Pharm Pharmacol. Apr. 1988;40(4):301-2.
Brookes, "The pharmacological treatment of Menière's disease." Clin Otolaryngol Allied Sci. Feb. 1996;21(1):3-11.
Kraut & Fauser, "Anti-emetics for cancer chemotherapy-induced emesis: Potential of alternative delivery systems." Drugs. 2001;61(11):1553-62.
Lehrer, "The use of antiserotonin drugs in the nucleoreticular vestibular syndrome: preliminary observations." Int Tinnitus J. 2004;10(1):84-6.
Ishiyama et al., "Histopathology of idiopathic chronic recurrent vertigo." Laryngoscope. Nov. 1996;106(11):1340-6.
Tsuji et al., "Temporal bone studies of the human peripheral vestibular system. Meniere's disease." Ann Otol Rhinol Laryngol Suppl. May 2000;181:26-31.
Malavasi Ganana et al., "Labyrinthopathies—Vestibular disorders" Revista Brasileira de Medicina vol. 61, No. Spec. ISS (Dec. 2004), 108-112).
Walker, "Treatment of vestibular neuritis." Curr Treat Options Neurol. Jan. 2009;11(1):41-5.
Strupp & Brandt, "Vestibular neuritis." Semin Neurol. Nov. 2009;29(5):509-19.
Khoo KS et al., 1993 "Use of oral and intravenous ondansetron in patients treated with cisplatin." Ann Acad Med Singapore. Nov. 1993;22(6):901-4 (abstract only).
Hui et al., "Prevention by the 5-HT3 receptor antagonist, ondansetron, of morphine-dependence and tolerance in the rat." Br J Pharmacol. Jun. 1996;118(4):1044-50.
International Search Report and Written Opinion, dated Jul. 18, 2017, from corresponding PCT application No. PCT/EP2017/059058.
Tucker et al., "Enantiomer specific pharmacokinetics", Pharmacology & Therapeutics, 1990, vol. 45, No. 3, pp. 309-329.
Tsukuda et al., "[A randomized crossover comparison of azasetron and granisetron in the prophylaxis of emesis induced by chemotherapy including cisplatin]", Gan To Kagaku Ryoho, Nov. 1995, vol. 22, No. 13, pp. 1959-1967—Abstract.

* cited by examiner

(+)-AZASETRON FOR USE IN THE TREATMENT OF EAR DISORDERS

FIELD OF INVENTION

The present invention relates to the field of ear disorders, in particular to methods for treating ear disorders. The present invention relates to (+)-azasetron, or pharmaceutically acceptable salts and/or solvates thereof, for use in the treatment of an ear disorder.

BACKGROUND OF INVENTION

In 2013, the world health organization estimated about 360 million persons (over 5% of the world's population) affected by an ear disorder due to diverse causes: noise, genetic conditions, complications at birth, certain infectious diseases, chronic ear infections, the use of particular drugs, and ageing. This number will increase with ageing population in the western countries and teenagers or young adults under increased exposure to unsafe level of noise.

The ear is comprised of three major structural components: the outer, middle, and inner ears, which function together to convert sound waves into nerve impulses that travel to the brain, where they are perceived as sound. The inner ear also helps to maintain balance.

The middle ear consists of the eardrum and a small air-filled chamber containing a sequence of three tiny bones known as the ossicles, which link the eardrum to the inner ear. The inner ear (labyrinth) is a complex structure consisting of the cochlea, which is the organ of hearing and the vestibular system, the organ of balance. The vestibular system consists of the saccule, the utricle, and the semicircular canals, which all help determine position and acceleration of the head in space and thus maintain balance.

The cochlea houses the organ of Corti, which consists, in part, of about 20,000 specialized sensory cells, called "inner ear hair cells" or "hair cells". These cells have small hairline projections (cilia) that extend into the cochlear fluid. Sound vibrations transmitted from the ossicles in the middle ear to the oval window in the inner ear cause the fluid and cilia to vibrate. Hair cells in different parts of the cochlea vibrate in response to different sound frequencies and convert the vibrations into nerve impulses which are sent to the brain for processing and interpretation. The inner ear hair cells are surrounded by inner ear support cells. Supporting cells underlie, at least partially surround, and physically support sensory hair cells within the inner ear. Representative examples of supporting cells include inner rod (pillar cells), outer rod (pillar cells), inner phalangeal cells, outer phalangeal cells (of Deiters), cells of Held, cells of Hensen, cells of Claudius, cells of Boettcher, interdental cells and auditory teeth (of Huschke).

The spiral ganglion is the group of nerve cells that send a representation of sound from the cochlea to the brain. The cell bodies of the spiral ganglion neurons are found in the spiral structure of the cochlea and are part of the central nervous system. Their dendrites make synaptic contact with the base of hair cells, and their axons are bundled together to form the auditory portion of the eighth cranial nerve (vestibulocochlear nerve).

Similarly, sensory hair cells in the vestibule respond to movements in inner ear fluids induced by head movements. The sensory hair cell responses are converted into nerve impulses in vestibular ganglion neurons through dendritic synaptic contacts from neurons to the base of vestibular hair cells. The vestibular neurons send representation of head position and movement in space to the brain through their axon bundles forming the vestibular portion of the vestibulocochlear nerve.

A variety of conditions may affect specifically one of these structures of the ear impairing hearing or balance: ear infections are the most common illness in infants and young children; tinnitus, a roaring in the ears, can be the result of loud noises, medicines or a variety of other causes; Meniere's disease may be the result of fluid problems in the inner ear, its symptoms include tinnitus and dizziness; ear barotrauma is an injury to the ear because of changes in barometric (air) or water pressure. Moreover, hearing loss and vertigo may be induced by drug-based ototoxicity, infections, trauma, ischemia or congenital causes. Such conditions may affect different parts of the ear.

Various pharmaceutical compounds have already been tested for the treatment of ear diseases: antibiotics, anti-inflammatory agents, or NMDA antagonists for example. Despite all the compounds tested, these drugs either exert strong adverse events, lack of efficacy, show an efficacy in the early symptoms only but no efficacy on chronic basis or show an efficacy on a small cohort of patients only. Therefore, there is a need to discover novel treatment for ear diseases that could be used for a wild range of persons.

In particular, the application WO2010/133663 provides evidence of compounds from the setron family including azasetron, for the treatment of lesional vestibular disorders.

The present application evidences that the enantiomer (+)-azasetron, or a pharmaceutically acceptable salt and/or solvate thereof, provides surprisingly good local drug exposure and results for the treatment of ear disorders, compared to racemic azasetron or enantiomer (−)-azasetron.

SUMMARY

One object of the invention is (+)-azasetron, of Formula (R)-I:

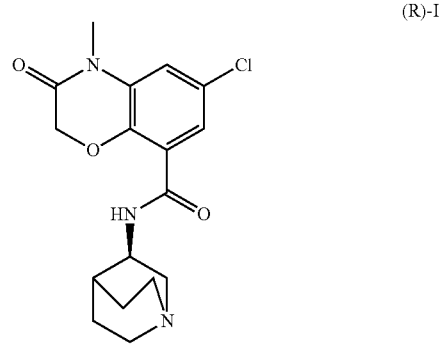 [SMILES: CN1C(=O)COc2c(C(=O)N[C@H]3CN4CCC3CC4)cc(Cl)cc21]

(R)-I or a pharmaceutically acceptable salt and/or solvate thereof, for use in the treatment of an ear disorder.

Another objection of the invention is a composition for use in the treatment of an ear disorder comprising (+)-azasetron, of Formula (R)-I:

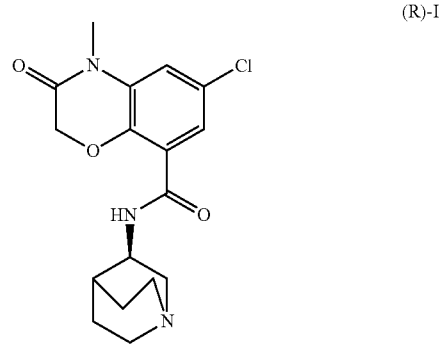 [SMILES: CN1C(=O)COc2c(C(=O)N[C@H]3CN4CCC3CC4)cc(Cl)cc21]

(R)-I or a pharmaceutically acceptable salt and/or solvate thereof; and at least one pharmaceutically acceptable excipient.

In one embodiment, the pharmaceutically acceptable salt is selected from (+)-azasetron besylate, (+)-azasetron malate and (+)-azasetron hydrochloride, and preferably is (+)-azasetron besylate.

In one embodiment, the composition is to be administered at a dose ranging from about 0.01 mg to about 100 mg of (+)-azasetron. In another embodiment, the composition is to be administered at a dose ranging from about 0.1 mg to about 100 mg of (+)-azasetron.

In one embodiment, the composition is to be administered systemically or locally, preferably systemically, more preferably orally.

In one embodiment, the ear disorder is selected from the group comprising: inner ear disorder, middle ear disorder, external ear disorder, infection of the ear, inflammation of the ear or autoimmune disorder of the ear. In one embodiment, the ear disorder is selected from hearing loss, tinnitus and a vestibular disorder.

In one embodiment, hearing loss is sensorineural hearing loss.

In one embodiment, sensorineural hearing loss is ototoxic compound-induced hearing loss, preferably platinum-induced hearing loss, more preferably cisplatin-induced hearing loss.

In one embodiment, the composition is to be administered to a subject diagnosed with cancer. In one embodiment, the subject diagnosed with cancer is awaiting the receipt of, or is receiving platinum-based chemotherapy, preferably cisplatin, carboplatin, oxaliplatin or a combination thereof. In one embodiment, the composition is to be administered before, during and/or after platinum-based chemotherapy, preferably cisplatin-, carboplatin- or oxaliplatin-based chemotherapy or a combination thereof.

In one embodiment, sensorineural hearing loss is sudden sensorineural hearing loss or noise-induced hearing loss.

In one embodiment, vestibular disorder is lesional vestibular disorder.

In one embodiment, the composition is an immediate release composition or a sustained release composition. In one embodiment, the composition is an orodispersible composition.

Definitions

In the present invention, the following terms have the following meanings:

"About" preceding a figure means plus or less 10% of the value of said figure.

"Pharmaceutically acceptable excipient" refers to an excipient that does not produce any adverse, allergic or other unwanted reactions when administered to an animal, preferably a human. It includes any and all solvents, dispersion media, coatings, antibacterial and antifungal agents, isotonic and absorption delaying agents and the like. For human administration, preparations should meet sterility, pyrogenicity, general safety, quality and purity standards as required by regulatory offices, such as, for example, FDA Office or EMA.

"Subject" refers to a mammal, preferably a human. In one embodiment, the subject is a pet, including, without limitation, a dog, a cat, a guinea pig, a hamster, a rat, a mouse, a ferret, a rabbit, a bird or an amphibian. In one embodiment, a subject may be a "patient", i.e., a female or a male, an adult or a child, who/which is awaiting the receipt of, or is receiving medical care or was/is/will be the object of a medical procedure, or is monitored for the development of an ear disease, disorder or condition.

"Therapeutically effective amount" refers to level or amount of agent that is aimed at, without causing significant negative or adverse side effects to the target, (1) delaying or preventing the onset of an ear disease, disorder, or condition; (2) slowing down or stopping the progression, aggravation, or deterioration of one or more symptoms of the ear disease, disorder, or condition; (3) bringing about ameliorations of the symptoms of the ear disease, disorder, or condition; (4) reducing the severity or incidence of the ear disease, disorder, or condition; or (5) curing the ear disease, disorder, or condition. A therapeutically effective amount may be administered prior to the onset of the ear disease, disorder, or condition, for a prophylactic or preventive action. Alternatively or additionally, the therapeutically effective amount may be administered after onset of the ear disease, disorder, or condition, for a therapeutic action. In one embodiment, a therapeutically effective amount of the composition is an amount that is effective in reducing at least one symptom of an ear disease, disorder or condition.

"Treating" or "treatment" or "alleviation" refers to both therapeutic treatment and prophylactic or preventative measures; wherein the object is to prevent or slow down (lessen) the targeted pathologic condition or disorder. Those in need of treatment include those already with the disorder as well as those prone to have the disorder or those in whom the disorder is to be prevented. A subject or mammal is successfully "treated" for the targeted pathologic disorder if, after receiving a therapeutic amount of the compound or composition of the present invention, the patient shows observable effects on one or more of the followings; (i) promotion of ear functioning; (ii) decrease in hearing loss; (iii) relief to some extent, of one or more of the symptoms associated with the specific disorder or condition, such as vertigo, dizziness and tinnitus; (iv) reduced morbidity and mortality, and (v) improvement in quality of life issues. The above parameters for assessing successful treatment and improvement in the disorder are readily measurable by routine procedures familiar to a physician.

"Prodrug" refers to the pharmacologically acceptable derivatives of compounds of Formula I of the invention, such as for example esters, whose in vivo biotransformation product generates the biologically active drug. Prodrugs are generally characterized by increased bio-availability and are readily metabolized into biologically active compounds in vivo.

"Predrug" refers to any compound that will be modified to form a drug species, wherein the modification may take place either inside or outside of the body, and either before or after the predrug reaches the area of the body where administration of the drug is indicated.

"Solvate" is used herein to describe a molecular complex comprising the compound of Formula I of the invention and one or more pharmaceutically acceptable solvent molecules, for example, ethanol. The term "hydrate" is employed when said solvent is water.

"Bioavailability" refers to the rate and extent to which a drug or other substance becomes available to the target tissue (i.e., reaches the target tissue), e.g., the inner ear, after administration.

"Vestibular disorders" refers to a vast family of conditions wherein the vestibular organ is associated. These disorders may be distinguished by their putative origins, one can thus identify (1) lesional vestibular disorders and (2) non lesional vestibular disorders.

"Lesional vestibular disorders" refer to vestibular disorders wherein lesions of inner ear cells and/or vestibular nerve are present or will appear during the disorder time course. In this case, the functionality of the vestibule is impaired. However, morphofunctional alterations of the vestibular endorgans cannot be evaluated directly (except for large lesions that can be detected by MRI). Conversely, indirect assessment methods are currently used to evaluate the loss of functionality of the vestibule. These testing methods are generally conducted at ENT clinic/hospitals. Among them we can cite the videonystagmography (VNG) and assessment of the vestibulo-ocular reflex (VOR) using caloric or rotational tests, video head impulse testing (vHIT) and vestibular evoked myogenic potentials (VEMP). Lesional vestibular disorders include:

- vestibular disorders wherein an inflammation of the inner ear and/or the vestibular nerve induces reversible and/or irreversible damages. Examples of conditions from this group include, but are not limited to, vestibular neuritis, acute unilateral vestibulopathy and vestibular neuronitis;
- vestibular disorders wherein inner ear fluids are affected (abnormalities in the quantity, composition, and/or pressure of the endolymph), these disorders usually develop lesions during the disease time course. Examples of conditions from this group are Meniere's disease and secondary endolymphatic hydrops. They are associated with tinnitus and hearing loss;
- vestibular disorders induced by insults or lesions of the vestibular endorgans. Examples of said conditions are vertigo caused by local ischemia, excitotoxicity, trauma that affect temporal bones or ototoxic insult to vestibular hair cells by drugs such as gentamicin and cisplatin;
- iterative vestibular disorders of unknown origin leading to permanent vestibular deficits, but without tinnitus or hearing loss. An example of a condition from this group is vestibular migraine (or migrainous vertigo).

"Non-lesional vestibular disorders" refer to vestibular disorders supported by transient and often iterative vertigo crisis wherein no lesion on inner ear cells and/or vestibular nerve can be observed. In this case, the functionality of the vestibule evaluated between the vertigo crisis using functional tests (VOR, VNG) does not differ from healthy vestibule. Non-lesional vestibular disorders include:

- vestibular disorders wherein debris had been collected within a part of the inner ear. This debris, called otoconia, is made up of small crystals of calcium carbonate and when they shift, they send false signals to the brain. Examples of said conditions include, but are not limited to, positional vertigos and in particular benign paroxysmal positional vertigo (BPPV);
- iterative vestibular disorders of unknown origin without tinnitus, hearing loss or permanent vestibular deficits.

DETAILED DESCRIPTION

One object of the invention is a compound of Formula I:

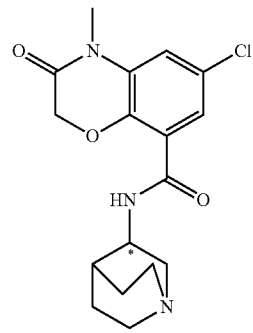

or a pharmaceutically acceptable salt and/or solvate thereof, wherein * stands for the (R)-enantiomer (corresponding to the (+)-enantiomer), the (S)-enantiomer (corresponding to the (−)-enantiomer), the racemate or a non-racemic mixture of (R) and (S) enantiomers (corresponding to mixtures of (+)- and (−)-enantiomers).

Compound of Formula I is called "azasetron" and corresponds to 6-chloro-3,4-dihydro-N-(8-methyl-8-azabicyclo-[3.2.1]-oct-3-yl)-2,4-dimethyl-3-oxo-2H-1,4-benzoxazine-8-carboxamide, which may also be referred to as N-(1-azabicyclo[2.2.2]octan-8-yl)-6-chloro-4-methyl-3-oxo-1,4-benzoxazine-8-carboxamide, as described in the U.S. Pat. No. 4,892,872, which is incorporated herein by reference.

Azasetron has one chiral center that can give rise to two stereoisomers.

In one embodiment, the invention refers to racemic azasetron, or a pharmaceutically acceptable salt and/or solvate thereof.

In one embodiment, the invention refers to the (R)-enantiomer of azasetron, or a pharmaceutically acceptable salt and/or solvate thereof. The (R)-enantiomer of azasetron is called (R)-azasetron or (+)-azasetron, corresponding to Formula (R)-I:

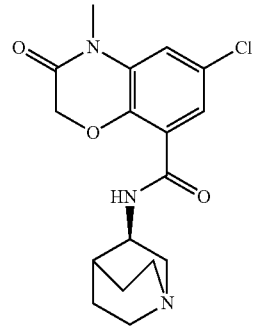

In one embodiment, the invention refers to the (S)-enantiomer of azasetron, or a pharmaceutically acceptable salt and/or solvate thereof. The (S)-enantiomer of azasetron is called (S)-azasetron or (−)-azasetron, corresponding to Formula (S)-I:

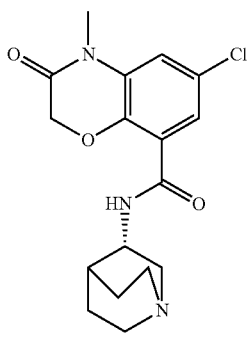

(S)-I

In a particularly preferred embodiment, the invention relates to (+)-azasetron, or a pharmaceutically acceptable salt and/or solvate thereof. Indeed, the Applicant surprisingly demonstrates that the administration of (+)-azasetron results in higher local exposure in the inner ear than racemic azasetron or (−)-azasetron. Therefore, bioavailability in the ear of (+)-azasetron is greater than that of racemic azasetron. In one embodiment, bioavailability in the ear of (+)-azasetron is at least 1.1, 1.2, 1.3, 1.4, 1.5, 1.6, 1.7, 1.8, 1.9, 2.0 or more times greater than that of racemic azasetron and/or (−)-azasetron.

The compounds of the invention include compounds of Formula I, preferably of Formula (R)-I as hereinbefore defined, including all polymorphs and crystal habits thereof, predrugs and prodrugs thereof and isotopically-labeled compounds of Formula I, preferably of Formula (R)-I.

The compounds of the invention may be in the form of pharmaceutically acceptable salts. Pharmaceutically acceptable salts of the compounds of Formula I include the acid addition salts thereof. Suitable acid addition salts are formed from acids which form non-toxic salts. Examples of acid addition salts include the besylate, hydrochloride/chloride, malate, benzoate, ethane-1,2-disulfonate, fumarate, tartrate, acetate, adipate, ascorbate, aspartate, bicarbonate/carbonate, bisulphate/sulphate, borate, camsylate, citrate, cyclamate, edisylate, esylate, ethanesulfonate, formate, gluceptate, gluconate, glucuronate, glutamate, hexafluorophosphate, hibenzate, hydrobromide/bromide, hydroiodide/iodide, isethionate, lactate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, p-toluenesulfonate, tosylate, trifluoroacetate and xinofoate salts.

In one embodiment, preferred acid addition salts include besylate, hydrochloride, malate, benzoate, ethane-1,2-disulfonate, fumarate and tartrate salts; more preferably besylate, hydrochloride, malate and benzoate salts; even more preferably besylate, hydrochloride or malate salts.

According to a specific embodiment, the invention relates to (+)-azasetron besylate, (+)-azasetron hydrochloride, (+)-azasetron malate, (+)-azasetron benzoate, (+)-azasetron ethane-1,2-disulfonate, (+)-azasetron fumarate and (+)-azasetron tartrate. According to a preferred embodiment, the invention relates to (+)-azasetron besylate, (+)-azasetron hydrochloride, (+)-azasetron malate, (+)-azasetron benzoate; more preferably the invention relates to (+)-azasetron besylate, (+)-azasetron hydrochloride or (+)-azasetron malate.

Pharmaceutically acceptable salts of compounds of Formula I may be prepared by reacting the compound of Formula I with the desired acid, or by converting one salt of the compound of Formula I to another by reaction with an appropriate acid or by means of a suitable ion exchange column. All these reactions are typically carried out in solution.

The salt may precipitate from solution and be collected by filtration or may be recovered by evaporation of the solvent. The degree of ionization in the salt may vary from completely ionized to not ionized resulting in a co-crystal.

Examples of processes that may be used to synthetize (+)-azasetron or a pharmaceutically acceptable salt and/or solvate thereof are well known in the art. Significant literature and background information is available on the synthesis of azasetron. Reference can be made, e.g., to Chinese patents CN101786963 and CN104557906.

In one embodiment, synthesis of (+)-azasetron or of a pharmaceutically acceptable salt and/or solvate thereof includes ab initio synthesis and/or chiral resolution.

In one embodiment, when ab initio synthesis of (+)-azasetron or of a pharmaceutically acceptable salt and/or solvate thereof is implemented, at least one racemic starting compound and/or intermediate compound is substituted by a chiral compound.

Another object of the invention is a composition comprising, consisting, or consisting essentially of at least one compound of Formula I or a pharmaceutically acceptable salt and/or solvate thereof.

Another object of the invention is a pharmaceutical composition comprising, consisting, or consisting essentially of at least one compound of Formula I or a pharmaceutically acceptable salt and/or solvate thereof and at least one pharmaceutically acceptable excipient.

Another object of the invention is a medicament comprising, consisting, or consisting essentially of at least one compound of Formula I or a pharmaceutically acceptable salt and/or solvate thereof.

In one embodiment, the composition, pharmaceutical composition or medicament of the invention comprises, consists or consists essentially of (+)-azasetron or a pharmaceutically acceptable salt and/or solvate thereof, preferably (+)-azasetron besylate, (+)-azasetron hydrochloride or (+)-azasetron malate.

As used herein, the term "consist essentially of", with reference to a composition, pharmaceutical composition or medicament, means that the at least one compound of the invention is the only one therapeutic agent or agent with a biologic activity within said composition, pharmaceutical composition or medicament.

In one embodiment, the composition, pharmaceutical composition or medicament of the invention does not comprise of (−)-azasetron or a pharmaceutically acceptable salt and/or solvate thereof. In one embodiment, the composition, pharmaceutical composition or medicament of the invention comprises less than about 40% w/w, 30% w/w, 20% w/w or 10% w/w of (−)-azasetron or a pharmaceutically acceptable salt and/or solvate thereof in weight to the total weight of azasetron, preferably less than about 9%, 8%, 7%, 6%, 5%, 4%, 3%, 2%, 1% w/w (−)-azasetron or a pharmaceutically acceptable salt and/or solvate thereof in weight to the total weight of azasetron, more preferably less than about 0.5%, 0.4%, 0.3%, 0.25%, 0.2%, 0.15%, 0.1% w/w (−)-azasetron or a pharmaceutically acceptable salt and/or solvate thereof in weight to the total weight of azasetron.

In one embodiment, the composition, pharmaceutical composition or medicament of the invention does not comprise a mixture of (+)-azasetron and (−)-azasetron, or pharmaceutically acceptable salts and/or solvates thereof.

In one embodiment, the composition, pharmaceutical composition or medicament of the invention comprises at least a 60:40 w/w mixture, preferably at least a 70: 30, 80: 20 or 90:10 w/w mixture of (+)-azasetron:(−)-azasetron, or pharmaceutically acceptable salts and/or solvates thereof, preferably at least a 95:5, 96:4, 97:3, 98:2, 99:1 w/w mixture of (+)-azasetron:(−)-azasetron, or pharmaceutically acceptable salts and/or solvates thereof, more preferably a 99.5: 0.5, 99.6:0.4, 99.7:0.3, 99.75:0.25, 99.8:0.2, 99.85:0.15, 99.9:0.1 w/w mixture of (+)-azasetron:(−)-azasetron, or pharmaceutically acceptable salts and/or solvates thereof.

Examples of pharmaceutically acceptable excipients include, but are not limited to, water, saline, Ringer's solution, dextrose solution, and solutions of ethanol, starch, glucose, sucrose, dextran, mannose, mannitol, sorbitol, polyethylene glycol (PEG), phosphate, acetate, gelatin, collagen, Carbopol®, vegetable oils, and the like. One may additionally include suitable preservatives, stabilizers, antioxidants, antimicrobials, and buffering agents, such as, for example, butylated hydroxyanisole (BHA), butylated hydroxytoluene (BHT), citric acid, ascorbic acid, tetracycline, and the like.

Carbopol® or "carbomer" refer to high molecular weight polymers of polyacrylic acid crosslinked with allyl sucrose or pentaerythritol allyl ether, said polymer comprising homopolymers and copolymers. Examples of Carbopol® include, but are not limited to, Carbopol® 910, Carbopol® 934, Carbopol® 940, Carbopol® 941, Carbopol® 974, Carbopol® 981, Carbopol® Ultrez and Polycarbophil.

Other examples of pharmaceutically acceptable excipients that may be used in the composition of the invention include, but are not limited to, ion exchangers, alumina, magnesium stearate, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

In addition, pharmaceutically acceptable excipients may also comprise, without limitation, surfactants (e.g. hydroxypropylcellulose); suitable carriers, such as, for example, solvents and dispersion media containing, for example, water, ethanol, polyol (e.g. glycerol, propylene glycol, and liquid polyethylene glycol, and the like), suitable mixtures thereof, and vegetable oils, such as, for example, peanut oil and sesame oil; isotonic agents, such as, for example, sugars or sodium chloride; coating agents, such as, for example, hydroxypropylmethylcellulose (HPMC), polyethylene glycol (PEG), polysorbate 80, titanium dioxide and lecithin; agents delaying absorption, such as, for example, aluminum monostearate and gelatin; preservatives, such as, for example, benzalkonium chloride, benzethonium chloride, chlorobutanol, thimerosal and the like; buffers, such as, for example, boric acid, sodium and potassium bicarbonate, sodium and potassium borates, sodium and potassium carbonate, sodium acetate, sodium biphosphate and the like; tonicity agents, such as, for example, dextrose, potassium chloride, propylene glycol, sodium chloride; antioxidants and stabilizers, such as, for example, sodium bisulfite, sodium metabisulfite, sodium thiosulfite, thiourea and the like; nonionic wetting or clarifying agents, such as, for example, polysorbate 80, polysorbate 20, poloxamer 282 and tyloxapol; viscosity modifying agents, such as, for example dextran 40, dextran 70, gelatin, glycerin, hydroxyethylcellulose, hydroxmethylpropylcellulose, lanolin, methylcellulose, petrolatum, polyethylene glycol, polyvinyl alcohol, polyvinylpyrrolidone, carboxymethylcellulose; diluents, adjuvants and the like.

Another object of the invention is a compound, a composition, a pharmaceutical composition or a medicament, as described hereinabove, for treating or for use in treating an ear disease, disorder or condition.

The present invention thus relates to (+)-azasetron or a pharmaceutically acceptable salt and/or solvate thereof (in particular (+)-azasetron besylate, (+)-azasetron hydrochloride, (+)-azasetron malate or a mixture thereof) as described hereinabove, for treating, or for use in treating an ear disease, disorder or condition.

In one embodiment, (+)-azasetron or a pharmaceutically acceptable salt and/or solvate thereof (in particular (+)-azasetron besylate, (+)-azasetron hydrochloride, (+)-azasetron malate or a mixture thereof) is for preventing an ear disease, disorder or condition. In another embodiment, (+)-azasetron or a pharmaceutically acceptable salt and/or solvate thereof (in particular (+)-azasetron besylate, (+)-azasetron hydrochloride, (+)-azasetron malate or a mixture thereof) is for alleviating a symptom or for curing an ear disease, disorder or condition.

The present invention also relates to a composition for treating an ear disease, disorder or condition, comprising or consisting of or consisting essentially of (+)-azasetron or a pharmaceutically acceptable salt and/or solvate thereof (in particular (+)-azasetron besylate, (+)-azasetron hydrochloride, (+)-azasetron malate or a mixture thereof).

In one embodiment, the composition of the invention is for preventing an ear disease, disorder or condition. In another embodiment, the composition of the invention is for alleviating a symptom of an ear disease, disorder or condition or for curing an ear disease, disorder or condition.

The present invention also relates to a pharmaceutical composition for treating an ear disease, disorder or condition, comprising or consisting of or consisting essentially of (+)-azasetron or a pharmaceutically acceptable salt and/or solvate thereof (in particular (+)-azasetron besylate, (+)-azasetron hydrochloride, (+)-azasetron malate or a mixture thereof) and at least one pharmaceutically acceptable excipient.

In one embodiment, the pharmaceutical composition of the invention is for preventing an ear disease, disorder or condition. In another embodiment, the pharmaceutical composition of the invention is for alleviating a symptom of an ear disease, disorder or condition or for curing an ear disease, disorder or condition.

The present invention also relates to a medicament for treating an ear disease, disorder or condition, comprising or consisting of or consisting essentially of (+)-azasetron or a pharmaceutically acceptable salt and/or solvate thereof (in particular (+)-azasetron besylate, (+)-azasetron hydrochloride, (+)-azasetron malate or a mixture thereof).

In one embodiment, the medicament of the invention is for preventing an ear disease, disorder or condition. In another embodiment, the medicament of the invention is for alleviating a symptom of an ear disease, disorder or condition or for curing an ear disease, disorder or condition.

In one embodiment, the compound, composition, pharmaceutical composition or medicament of the invention is for treating ear diseases, disorders or conditions selected from the group comprising, but not limited to, cochlear diseases, disorders or conditions; vestibular diseases, disorders or conditions; inner ear diseases, disorders or conditions; middle ear diseases, disorders or conditions; external ear diseases, disorders or conditions; infection of the ear; and inflammation of the ear.

In one embodiment, the compound, composition, pharmaceutical composition or medicament of the invention is for treating cochlear diseases, disorders or conditions, including without limitation, hearing loss, tinnitus, cochlear ototoxicity (i.e., toxicity inducing damages of the cochlea), cochlear excitotoxic-inducing occurrence, head trauma with cochlear lesion, cochlear hyperacusis, and cochlear tinnitus.

In one embodiment, the compound, composition, pharmaceutical composition or medicament of the invention is for treating hearing loss, including without limitation, sensorineural hearing loss, conductive hearing loss and mixed hearing loss (wherein mixed hearing loss is a combination of both sensorineural and conductive hearing loss).

Sensorineural hearing loss and conductive hearing loss may be distinguished according to tests well known of the skilled artisan, including, without limitation, Weber and Rinne tests, otoscopy, audiograms, audiometry, auditory brainstem recordings, optoacoustic emissions recordings, word recognition tests and speech-in-noise tests.

Methods for measuring hearing loss are well-known by the skilled artisan. Examples of such methods include, but are not limited to, tympanometry, acoustic reflex tests, tuning fork test, bone conduction test, pure tone audiogram, behavioral observation audiometry, visual reinforcement audiometry, conditioned play audiometry, ABR (auditory brainstem responses) measurement, DPOAE (distortion product otoacoustic emissions) measurement, TEOAE (transiently evoked otoacoustic emissions) measurement, speech in noise test, word comprehension test and the like.

In one embodiment, the compound, composition, pharmaceutical composition or medicament of the invention is for treating sensorineural hearing loss including, without limitation, sudden sensorineural hearing loss (e.g., idiopathic sudden hearing loss), noise-induced sensorineural hearing loss, drug-induced sensorineural hearing loss (e.g., ototoxic compound-induced hearing loss), acquired sensorineural hearing loss, age-related hearing loss, congenital, hereditary and genetic sensorineural hearing loss (such as, but not limited to, Usher syndrome, Pendred syndrome, Jervell and Lange-Nielsen syndrome, Alport syndrome, Mohr-Tranebjaerg syndrome and Cogan syndrome) (i.e., sensory hair cells, neurons and supporting cells of the cochlea or the auditory nerve were abnormal at birth or become abnormal during development) and sensorineural hearing loss induced by viral or bacterial infection (such as, but not limited to, CMV).

Examples of causes of sensorineural hearing loss include, but are not limited to, ototoxic compounds, excessive noise exposure (such as, for example, exposure to a noise of more than about 70 dB, 80 dB, 90 dB, 100 dB, 110 dB, 120 dB, 130 dB or more), aging, inflammation, inner ear involvement by infectious agents (such as, for example, viral and bacterial infections), autoimmunity (such as, for example, autoimmune inner ear disease) or vasculopathy, illnesses (including but not limited to high blood pressure and diabetes), head trauma, tumors or blast exposure.

Examples of ototoxic compounds that may cause sensorineural hearing loss include, but are not limited to, chemotherapeutic agents (such as, without limitation, platinum drugs, including, without limitation, cisplatin, carboplatin, oxaliplatin, satraplatin, picoplatin, tetraplatin, transplatin, nedaplatin, ormaplatin, PtCl$_2$[R,RDACH], pyriplatin, ZD0473, BBR3464 and Pt-1C3), aminoglycosides (such as, but not limited to, neomycin, gentamycin, kanamycin, amikacin and tobramycin), loop diuretics (such as, without limitation, furosemide, torsemide and bumetanide), macrolides (such as, without limitation, erythromycin and azithromycin), glycopeptides (such as, without limitation, vancomycin) antimetabolites (such as, without limitation, methotrexate), antimalarials (such as, without limitation, quinine), antiretroviral drugs (such as, without limitation, abacavir, AZT, delavirdine, didenosine, efavirenz, emtricitabine, indinavir, lamivudine, nefinavir, nevirapine, tenofovir, ritonavir, stavudine and zalcitabine) and salicylates (such as, without limitation, aspirin).

In one embodiment, the compound, composition, pharmaceutical composition or medicament of the invention is for treating ototoxic compound-induced sensorineural hearing loss. In one embodiment, the compound, composition, pharmaceutical composition or medicament of the invention is for treating chemotherapeutic agents-induced sensorineural hearing loss. In one embodiment, the compound, composition, pharmaceutical composition or medicament of the invention is for treating platinum-induced sensorineural hearing loss, such as, without limitation, sensorineural hearing loss induced by cisplatin, carboplatin, oxaliplatin, satraplatin, picoplatin, tetraplatin, transplatin, nedaplatin, ormaplatin, PtCl$_2$[R,RDACH], pyriplatin, ZD0473, BBR3464 and/or Pt-1C3, preferably cisplatin.

In one embodiment, the compound, composition, pharmaceutical composition or medicament of the invention is for treating compound-induced ototoxicity, including without limitation, ototoxicity induced by chemotherapeutic agents (such as, without limitation, platinum drugs, including, without limitation, cisplatin, carboplatin, oxaliplatin, satraplatin, picoplatin, tetraplatin, transplatin, nedaplatin, ormaplatin, PtCl$_2$[R,RDACH], pyriplatin, ZD0473, BBR3464 and Pt-1C3), aminoglycosides (such as, but not limited to, neomycin, gentamycin, kanamycin, amikacin and tobramycin), loop diuretics (such as, without limitation, furosemide, torsemide and bumetanide), macrolides (such as, without limitation, erythromycin and azithromycin), glycopeptides (such as, without limitation, vancomycin) antimetabolites (such as, without limitation, methotrexate), antimalarials (such as, without limitation, quinine and analogs thereof), salicylates and analogs thereof (such as, without limitation, aspirin), radiation treatment, antibiotic agents, excitatory neurotoxins, immunosuppressive agents, β-blockers, vasodilator agents, anti-retroviral drugs (such as, without limitation, abacavir, AZT, delavirdine, didenosine, efavirenz, emtricitabine, indinavir, lamivudine, nefinavir, nevirapine, tenofovir, ritonavir, stavudine and zalcitabine), cardiovascular agents (e.g. ACE inhibitors), antiplatelet agents, radiocontrast media, immunoglobulins, mannitol, NSAIDs, heavy metals, lithium salts, catechol-O-methyl-transferase inhibitors, antiepileptic drugs, proton pump inhibitors, antidepressants, antihistamines (e.g. diphenhydramine, doxylamine), antibacterial sulfonamides, benzodiazepines, pesticides, neurotoxic agents (e.g. glutamate, Bicuculline, Botulinum toxin), alcohol, heavy metals, and drugs of abuse (e.g. cocain, heroin, ketamine). In one embodiment, the compound, composition, pharmaceutical composition or medicament of the invention is for treating radiation treatment-induced ototoxicity.

Examples of inflammatory causes of sensorineural hearing loss include, but are not limited to, autoinflammatory diseases (such as, for example, Muckle-Wells Syndrome), suppurative labyrinthitis, meningitis, mumps or measles.

Examples of viral causes of sensorineural hearing loss include, but are not limited to, syphilis, mumps or measles.

In one embodiment, the compound, composition, pharmaceutical composition or medicament of the invention is for treating sudden hearing loss, preferably sudden sensorineural hearing loss (SSNHL).

Sudden hearing loss may be defined by the following audiometric criterion: decrease in hearing of at least about 10 dB, 20 dB, 30 dB or more over at least three contiguous frequencies, evolving within 3 days or less. Because pre-morbid audiometry is generally unavailable, for unilateral hearing loss, hearing loss may be defined as relative to the opposite ear's thresholds or relative to population means.

Sudden hearing loss, preferably sudden sensorineural hearing loss (SSNHL), may result (without limitation) from vestibular schwannoma (acoustic neuroma), stroke, malignancy, vascular ischemia of the inner ear, perilymph fistula or autoimmune causes (including, without limitation, IgE or IgG allergy) or other causes (such as, for example, causes listed above). However, a cause of SSNHL is identified in only 10 to 15% of patients at the time of presentation.

In one embodiment, the compound, composition, pharmaceutical composition or medicament of the invention is for treating acquired sensorineural hearing loss, i.e., sensory hair cells, synapses and neurons of the cochlea or the auditory nerve were normal at birth, but were subsequently damaged.

In one embodiment, the compound, composition, pharmaceutical composition or medicament of the invention is for treating congenital hearing loss, preferably congenital sensorineural hearing loss including, including, without limitation, a lack of development (aplasia) of the cochlea, chromosomal syndromes, hereditary hearing loss (such as, but not limited to, Usher syndrome, Pendred syndrome, Jervell and Lange-Nielsen syndrome, Alport syndrome, Mohr-Tranebjaerg syndrome and Cogan syndrome), congenital cholesteatoma, delayed familial progressive, congenital rubella syndrome, and human Cytomegalovirus (HCMV) transmission to a developing fetus during pregnancy.

In one embodiment, the compound, composition, pharmaceutical composition or medicament of the invention is for treating conductive hearing loss, resulting from abnormalities of the external ear, tympanic membrane, middle ear space or ossicles. It may result from cerumen impaction, middle ear fluid, otitis media, foreign bodies, perforated tympanic membrane, canal edema from otitis externa, otosclerosis, trauma (such as loss of residual hearing from electrode insertion trauma in cochlear implant surgery or surgery-induced hearing loss) or cholesteatoma (all these conditions may be diagnosed by otoscopy).

In one embodiment, the compound, composition, pharmaceutical composition or medicament of the invention is for treating tinnitus. In one embodiment, tinnitus is a symptom of hearing loss.

In one embodiment, the compound, composition, pharmaceutical composition or medicament of the invention is for treating vestibular diseases, disorders or conditions, including without limitation, lesional vestibular disorders and non-lesional vestibular disorders.

In one embodiment, the compound, composition, pharmaceutical composition or medicament of the invention is for treating vestibular diseases, disorders or conditions, including without limitation, vestibular migraine, vestibular neuritis (including, without limitation, vestibular neuronitis, viral neuronitis, labyrinthitis, viral endolymphatic labyrinthitis, serous labyrinthitis, suppurative labyrinthitis), acute unilateral vestibulopathy, vertigo and dizziness (including, without limitation, migraine-associated vertigo, spontaneous episodic vertigo, benign positional paroxysmal vertigo, familial episodic vertigo, age-related dizziness and imbalance, motion sickness, mal de debarquement), vestibular ototoxicity (including, without limitation, compound-induced and drug-induced ototoxicity, i.e., inducing impairment of the vestibule function leading to vestibular deficits, and induced by compounds listed without limitation above), vestibule-toxic impairments, hydrops (including, without limitation, endolymphatic hydrops, secondary endolymphatic hydrops), Méniére's disease (including, without limitation, spell of Menibre's disease, chronic Méniëre disease), fistula (including, without limitation, perilymphatic fistula, labyrinthine fistula), trauma (including, without limitation, head trauma with labyrinthine haemorrhage, barotrauma), infections (including, without limitation, chronic or acute labyrinthine infection), autoimmune inner ear disease, benign or malignant tumors (including, without limitation, vestibular schwannomas, acoustic neuroma), presbyvestibula, vestibular syndromes after chirurgical treatments of middle ear, channelopathies, superior semicircular canal dehiscence, endolymphatic sac or pontocerebellar angle, ataxia (including, without limitation, episodic ataxia), enlarged vestibular aqueduct, bilateral vestibular hypofunction, neurotoxic vestibulopathy, pediatric vestibular disorder, Cogan syndrome, vestibular hyperacusis, vertebrobasilar insufficiency.

In one embodiment, the compound, composition, pharmaceutical composition or medicament of the invention is for treating lesional vestibular diseases, disorders or conditions, including without limitation, vestibular migraine, vestibular neuritis (including, without limitation, vestibular neuronitis, viral neuronitis, labyrinthitis, viral endolymphatic labyrinthitis, serous labyrinthitis, suppurative labyrinthitis), acute unilateral vestibulopathy, vertigo and dizziness (including, without limitation, migraine-associated vertigo, spontaneous episodic vertigo, familial episodic vertigo, age-related dizziness and imbalance), vestibular ototoxicity (including, without limitation, compound-induced and drug-induced ototoxicity, i.e., inducing impairment of the vestibule function leading to vestibular deficits, and induced by compounds listed without limitation above), vestibule-toxic impairments, hydrops (including, without limitation, endolymphatic hydrops, secondary endolymphatic hydrops), Menibre's disease (including, without limitation, spell of Menibre's disease, chronic Menibre disease), fistula (including, without limitation, perilymphatic fistula, labyrinthine fistula), trauma (including, without limitation, head trauma with labyrinthine haemorrhage, barotrauma), infections (including, without limitation, chronic or acute labyrinthine infection), autoimmune inner ear disease, benign or malignant tumors (including, without limitation, vestibular schwannomas, acoustic neuroma), presbyvestibula, vestibular syndromes after chirurgical treatments of middle ear, channelopathies, superior semicircular canal dehiscence, endolymphatic sac or pontocerebellar angle, ataxia (including, without limitation, episodic ataxia), enlarged vestibular aqueduct, bilateral vestibular hypofunction, neurotoxic vestibulopathy, pediatric vestibular disorder, Cogan syndrome, vestibular hyperacusis, vertebrobasilar insufficiency.

In one embodiment, the compound, composition, pharmaceutical composition or medicament of the invention is for treating non-lesional vestibular diseases, disorders or conditions, including without limitation, benign positional paroxysmal vertigo, motion sickness and mal de debarquement.

Methods to determine if a disease, disorder or condition is a lesional vestibular disease, disorder or condition, i.e., if the functionality of the vestibule is impaired, include MRI for identifying large lesions or indirect assessment methods allowing the evaluation of the loss of functionality of the vestibule. These methods are generally conducted at ENT clinic/hospitals and include the videonystagmography (VNG), and assessment of the vestibulo-ocular reflex (VOR) using caloric or rotational tests. The function of the vestibulo-ocular reflex (VOR) is to stabilize the visual image on the retina during displacement. Measurement of this VOR provides convenient method to investigate the functionality of the vestibular system. Basically, the paradigm in based on monitoring eyes movements by infrared light projection technique (Sergi et al., "Cisplatin ototoxicity in the guinea pig: vestibular and cochlear damage". Hear Res. 2003 August; 182(1-2):56-64). Patients are sinusoidally oscillated in the dark around their vertical and longitudinal axes in order to evoke horizontal and vertical eye responses. Any functional impairment of the vestibule is associated with alterations in the gain of the evoked VNG. Besides VOR and VNG, posturography methods are used to detect postural deviations of the body that are also related to impairments of the vestibule. Morphofunctional investigations such as functional imaging (MRI or CAT (computerized axial tomography) and derivates) can be used to detect profound lesions within the vestibular endorgans. Specifically adapted VNG, VOR and postural testing are used in animal models of vestibular deficits to evaluate the amplitude of the insults or lesions in the vestibule. Histological studies are also possible using conventional light or electron microscopy on fixed tissue (vestibular ganglia and vestibular endorgans). Such investigations are mostly done in rodents.

In one embodiment, the compound, composition, pharmaceutical composition or medicament of the invention is for treating inner ear diseases, disorders or conditions, including without limitation, ototoxicity (including, without limitation, compound-induced ototoxicity), infection of the inner ear, trauma (including, without limitation, trauma of the inner ear, blunt or blast-induced head trauma leading to inner ear damage), tumors of the inner ear, inner ear inflammation, inner ear cell degeneration or age-induced inner ear cell degeneration, autoimmune ear disorder, cochlear disorder, vestibular disorder, Meniere's disease (including, without limitation, spell of Meniere's disease, chronic Meniere disease), neuritis (including, without limitation, vestibular neuritis, vestibular neuronitis, labyrinthitis), acute unilateral vestibulopathy, vestibular migraine, migrainous vertigo, otitis media (including, without limitation, chronic otitis media, acute otitis media, serous otitis media (otitis media with effusion), acute and chronic suppurative otitis media), mastoiditis (including, without limitation, acute and chronic mastoiditis), perforation of the eardrum (tympanic membrane), otosclerosis, superior semicircular canal dehiscence syndrome, otalgia, tinnitus, myoclonus, and mal de debarquement.

In one embodiment, the compound, composition, pharmaceutical composition or medicament of the invention is for treating middle ear diseases, disorders or conditions, including without limitation, hearing loss, tinnitus, infection of the middle ear, Meniere's disease (including, without limitation, spell of Meniere's disease, chronic Meniere disease), otitis media (including, without limitation, chronic otitis media, acute otitis media, serous otitis media (otitis media with effusion), acute and chronic suppurative otitis media), mastoiditis (including, without limitation, acute and chronic mastoiditis), adenoid hypertrophy, neoplasia, intratubal obstruction, middle ear obstruction, perforation of the eardrum (tympanic membrane), cholesteatoma (congenital, primary acquired, secondary acquired), CANVAS syndrome, tympanosclerosis, trauma (including, without limitation, trauma of the middle ear, temporal bone fractures, barotrauma, head trauma, blast-induced trauma), benign and malignant tumors (including, without limitation, tumors of the middle ear, glomus tumors, auditory nerve tumor (i.e., acoustic neuroma, acoustic neurinoma, vestibular schwannoma, eighth nerve tumor), malignant neoplasia including squamous cell carcinoma), and otalgia.

In one embodiment, the compound, composition, pharmaceutical composition or medicament of the invention is for treating external ear diseases, disorders or conditions, including without limitation, infection of the external ear, allergy of the external ear, trauma of the external ear, cysts, tumors, otitis externa ("swimmer's ear"), acute otitis extema, chronic otitis extema, suppurative otitis extema, necrotizing external otitis, otomycosis, perichondritis, bullous myringitis, granular myringitis, herpes zoster oticus (Ramsey Hunt syndrome), contact dermatitis, ear eczema, lacerations of the external canal, presence of foreign bodies, pilar (sebaceous) cysts, epidermal cysts, benign lesions including exostosis and malignant lesions including basal cell epithelioma, squamous cell carcinoma and otalgia.

In one embodiment, the compound, composition, pharmaceutical composition or medicament of the invention is for treating inflammation of the ear include without limitation, inner ear inflammation, autoimmune ear disorder, inflammation of the middle ear, otitis media (including, without limitation, chronic otitis media, acute otitis media, serous otitis media (otitis media with effusion), acute and chronic suppurative otitis media), Muckle-Wells Syndrome, suppurative labyrinthitis, meningitis, mumps or measles.

In one embodiment, the subject is a mammal. In one embodiment, the subject is a pet, such as a dog, a cat, a guinea pig, a hamster, a rat, a mouse, a ferret, a rabbit, a bird or an amphibian. In one embodiment, the subject is a human.

In one embodiment, the subject is a male. In one embodiment, the subject is a female.

In one embodiment, the subject is an adult, i.e., a subject aged 18 or more (in human years). In one embodiment, the subject is a teenager, i.e., a subject aged from 12 to 18 (in human years), such as a subject aged 12, 13, 14, 15, 16, 17 (in human years). In one embodiment, the subject is a child, i.e., a subject aged below 12 (in human years), such as a subject aged 1, 2, 3, 4, 5, 6, 7, 8, 9, 10, 11 (in human years).

In one embodiment, the subject is an adult weighting from about 40 to about 100 kg or more. In one embodiment, the subject in a teenager weighting from about 20 to about 80 kg or more. In one embodiment, the subject is a child weighting from about 1 to about 40 kg or more.

In one embodiment, the subject is awaiting the receipt of, or is receiving medical care or was/is/will be the object of a medical procedure, or is monitored for the development of an ear disease, disorder or condition.

In one embodiment, the subject is/was diagnosed with cancer.

Examples of cancers include, but are not limited to, neuroblastoma, hepatoblastoma, medulloblastoma, osteosarcoma, malignant germ cell tumour, nasopharyngeal carcinoma, lung cancer, colon cancer, breast cancer, ovarian cancer, prostate cancer, testicular cancer, stomach cancer, kidney cancer, liver cancer, bladder cancer, esophageal cancer, brain cancer, head and neck cancer, bone cancer, and leukemia.

In one embodiment, the subject is awaiting the receipt of, or is receiving chemotherapy.

Chemotherapy refers to course of treatment wherein a chemotherapeutic agent is administered to an individual diagnosed with a cancer. A chemotherapeutic agent includes agents such as drugs which can advantageously be administered to an individual with cancer, to treat said cancer. Examples of chemotherapy include, but are not limited to, platinum-based chemotherapy and non-platinum-based chemotherapy.

Examples of platinum-based chemotherapy include, but are not limited to, cisplatin, carboplatin, oxaliplatin, satraplatin, picoplatin, tetraplatin, transplatin, nedaplatin, ormaplatin, $PtCl_2[R,RDACH]$, pyriplatin, ZD0473, BBR3464 and Pt-1C3.

Examples of non-platinum-based chemotherapy include, but are not limited to, nucleoside analogues, antifolates, topoisomerase I inhibitors, anthracyclines, podophyllotoxins, taxanes, vinca alkaloids, alkylating agents, monoclonal antibodies, tyrosine kinase inhibitor, mTOR inhibitors, retinoids, immunomodulatory agents, histone deacetylase inhibitors and the like.

In one embodiment, the subject is/was diagnosed with cancer and is awaiting the receipt of, or is receiving platinum-based chemotherapy, preferably cisplatin, carboplatin, oxaliplatin or a combination thereof.

In one embodiment, the subject is awaiting receipt of, or is receiving aminoglycosides (such as, but not limited to, neomycin, gentamycin, kanamycin, amikacin and tobramycin), loop diuretics (such as, without limitation, furosemide, torsemide and bumetanide), macrolides (such as, without limitation, erythromycin and azithromycin), glycopeptides (such as, without limitation, vancomycin) antimetabolites (such as, without limitation, methotrexate), antimalarials (such as, without limitation, quinine and analogs thereof), salicylates and analogs thereof (such as, without limitation, aspirin), radiation treatment, antibiotic agents, excitatory neurotoxins, immunosuppressive agents, β-blockers, vasodilator agents, anti-retroviral drugs (such as, without limitation, abacavir, AZT, delavirdine, didenosine, efavirenz, emtricitabine, indinavir, lamivudine, nefinavir, nevirapine, tenofovir, ritonavir, stavudine and zalcitabine), cardiovascular agents (e.g. ACE inhibitors), antiplatelet agents, radiocontrast media, immunoglobulins, mannitol, NSAIDs, heavy metals, lithium salts, catechol-O-methyltransferase inhibitors, antiepileptic drugs, proton pump inhibitors, antidepressants, antihistamines (e.g. diphenhydramine, doxylamine), antibacterial sulfonamides, benzodiazepines, pesticides, neurotoxic agents (e.g. glutamate, Bicuculline, Botulinum toxin) or a combination thereof.

In one embodiment, the subject uses or is exposed or is at risk of being exposed to, alcohol, heavy metals, drugs (e.g. cocaine, heroin, ketamine) or a combination thereof.

In one embodiment, the compound of Formula (I) or a pharmaceutically acceptable salt and/or solvate thereof, preferably (+)-azasetron or a pharmaceutically acceptable salt and/or solvate thereof, preferably (+)-azasetron besylate, (+)-azasetron hydrochloride or (+)-azasetron malate; or the composition comprising thereof, pharmaceutical composition comprising thereof or medicament comprising thereof, is to be administered at a dose determined by the skilled artisan and personally adapted to each subject.

In one embodiment of the invention, the compound of Formula (I) or a pharmaceutically acceptable salt and/or solvate thereof, preferably (+)-azasetron or a pharmaceutically acceptable salt and/or solvate thereof, preferably (+)-azasetron besylate, (+)-azasetron hydrochloride or (+)-azasetron malate; or the composition comprising thereof, pharmaceutical composition comprising thereof or medicament comprising thereof is to be administered at a therapeutically effective amount.

It will be understood that the total daily usage of the compound of Formula (I) or a pharmaceutically acceptable salt and/or solvate thereof, preferably (+)-azasetron or a pharmaceutically acceptable salt and/or solvate thereof, preferably (+)-azasetron besylate, (+)-azasetron hydrochloride or (+)-azasetron malate; or of the composition comprising thereof, pharmaceutical composition comprising thereof or medicament comprising thereof will be decided by the attending physician within the scope of sound medical judgment. The specific therapeutically effective dose level for any particular patient will depend upon a variety of factors including the disorder being treated and the severity of the disorder; activity of the specific compound employed; the specific composition employed, the age, body weight, general health, sex and diet of the patient; the time of administration, route of administration, and rate of excretion of the specific compound employed; the duration of the treatment; drugs used in combination or coincidental with the specific composition employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the compound of Formula (I) or a pharmaceutically acceptable salt and/or solvate thereof, preferably (+)-azasetron or a pharmaceutically acceptable salt and/or solvate thereof, preferably (+)-azasetron besylate, (+)-azasetron hydrochloride or (+)-azasetron malate may be varied over a wide range from about 0.1 to about 10000 mg per adult per day, preferably 0.1 to about 2000, more preferably from about 0.1 to about 500 mg per adult per day, more preferably from about 0.1 to about 100 mg per adult per day.

Preferably, the compositions contain 0.1, 0.5, 1, 10, 20, 50, 100, 250, 500, 1000 or 2,000 mg of the compound of Formula (I) or a pharmaceutically acceptable salt and/or solvate thereof, preferably (+)-azasetron or a pharmaceutically acceptable salt and/or solvate thereof, preferably (+)-azasetron besylate, (+)-azasetron hydrochloride or (+)-azasetron malate, for the symptomatic adjustment of the dosage to the patient to be treated. In one embodiment, quantities of Formula (I) compound, preferably of (+)-azasetron, are expressed as free-base equivalent. Therefore, in one embodiment, the compositions contain 1, 5, 10, 15, 20, 25, 30, 35, 40, 45, 50, 55, 60, 65, 70, 75, 80, 85, 90, 95 or 100 mg of the free-base compound of Formula (I), preferably of free-base (+)-azasetron. In one embodiment, quantities of Formula (I) compound, preferably of (+)-azasetron, are expressed as salt and/or solvate equivalent. Therefore, in one embodiment, the compositions contain 1, 5, 10, 15, 20, 25, 30, 35, 40, 45, 50, 55, 60, 65, 70, 75, 80, 85, 90, 95, 100, 105, 110, 115, 120 or 125 mg of a pharmaceutically acceptable salt and/or solvate of the compound of Formula (I), preferably of a pharmaceutically acceptable salt and/or solvate of (+)-azasetron, preferably (+)-azasetron besylate, (+)-azasetron hydrochloride or (+)-azasetron malate.

A medicament may typically contain from about 0.1 to about 10000 mg of the compound of Formula (I) or a pharmaceutically acceptable salt and/or solvate thereof, preferably (+)-azasetron or a pharmaceutically acceptable salt and/or solvate thereof, preferably (+)-azasetron besylate, (+)-azasetron hydrochloride or (+)-azasetron malate, preferably from about 0.1 to about 2000 mg, more preferably from about 0.1 to about 500 mg, more preferably from about 0.1 to about 100 mg of the compound of Formula (I) or a pharmaceutically acceptable salt and/or solvate thereof, preferably (+)-azasetron or a pharmaceutically acceptable salt and/or solvate thereof, preferably (+)-azasetron besylate, (+)-azasetron hydrochloride or (+)-azasetron malate. In one embodiment, quantities of Formula (I) compound, preferably of (+)-azasetron, are expressed as free-base equivalent. Therefore, in one embodiment, the medicament contains 1, 5, 10, 15, 20, 25, 30, 35, 40, 45, 50, 55, 60, 65, 70, 75, 80, 85, 90, 95 or 100 mg of the free-base compound of Formula (I), preferably of free-base (+)-azasetron. In one embodiment, quantities of Formula (I) compound, preferably of (+)-azasetron, are expressed as salt and/or solvate equivalent. Therefore, in one embodiment, the medicament contains 1, 5, 10, 15, 20, 25, 30, 35, 40, 45, 50, 55, 60, 65, 70, 75, 80, 85, 90, 95, 100, 105, 110, 115, 120 or 125 mg of a pharmaceutically acceptable salt and/or solvate of the compound of Formula (I), preferably of a pharmaceutically acceptable salt and/or solvate of (+)-azasetron, preferably (+)-azasetron besylate, (+)-azasetron hydrochloride or (+)-azasetron malate.

An effective amount of the free-base compound of Formula (I) or a pharmaceutically acceptable salt and/or solvate thereof, preferably free-base (+)-azasetron or a pharmaceutically acceptable salt and/or solvate thereof, preferably (+)-azasetron besylate, (+)-azasetron hydrochloride or (+)-azasetron malate may ordinarily be supplied at a dosage level from about 0.01 mg/kg to about 100 mg/kg of body weight per day, preferably from about 0.02 mg/kg to 20 mg/kg of body weight per day, more preferably from about 0.05 mg/kg to 5 mg/kg of body weight per day, more preferably from about 0.1 mg/kg to 2 mg/kg of body weight per day, more preferably at about 0.5 mg/kg of body weight per day. In one embodiment, effective amounts of Formula (I) compound, preferably of (+)-azasetron, are expressed as free-base equivalent. In one embodiment, quantities of Formula (I) compound, preferably of (+)-azasetron, are expressed as salt and/or solvate equivalent.

In one embodiment, the dosage of the free-base compound of Formula (I), preferably free-base (+)-azasetron ranges from about 0.1 to about 500 mg of free-base equivalent per adult per day, preferably from about 1 to about 200 mg, more preferably from about 10 to about 100 mg, more preferably from about 30 to about 60 mg of free-base equivalent per adult per day. In one embodiment, the dosage of a pharmaceutically acceptable salt and/or solvate of the compound of Formula (I), preferably a pharmaceutically acceptable salt and/or solvate of (+)-azasetron, preferably (+)-azasetron besylate, (+)-azasetron hydrochloride or (+)-azasetron malate, ranges from about 0.1 to about 500 mg of salt and/or solvate equivalent per adult per day, preferably from about 1 to about 200 mg, more preferably from about 10 to about 100 mg, more preferably from about 43 to about 87 mg of salt and/or solvate equivalent per adult per day.

In one embodiment, the subject is a preterm newborn, a term newborn, a child and/or a teenager. In one embodiment, the subject is/was diagnosed with cancer. In one embodiment, the subject is awaiting receipt of or is receiving chemotherapy, preferably platinum-based chemotherapy, more preferably cisplatin-based chemotherapy. Then, in one embodiment, an effective amount of the compound of Formula (I) or a pharmaceutically acceptable salt and/or solvate thereof, preferably (+)-azasetron or a pharmaceutically acceptable salt and/or solvate thereof, preferably (+)-azasetron besylate, (+)-azasetron hydrochloride or (+)-azasetron malate may ordinarily be supplied at a dosage level from about 0.1 mg/kg to about 2 mg/kg, preferably from about 0.2 mg/kg to about 1 mg/kg, more preferably about 0.5 mg/kg. In one embodiment, the maximum daily dosage of the free-base compound of Formula (I), preferably free-base (+)-azasetron ranges from about 0.1 to about 500 mg of free-base equivalent per day, preferably from about 1 to about 200 mg, more preferably from about 10 to about 100 mg, more preferably from about 30 to about 60 mg of free-base equivalent per day. In one embodiment, the maximum daily dosage of a pharmaceutically acceptable salt and/or solvate of the compound of Formula (I), preferably a pharmaceutically acceptable salt and/or solvate of (+)-azasetron, preferably (+)-azasetron besylate, (+)-azasetron hydrochloride or (+)-azasetron malate ranges from about 0.1 to about 500 mg of salt and/or solvate equivalent per day, preferably from about 1 to about 200 mg, more preferably from about 10 to about 100 mg, more preferably from about 43 to about 87 mg of salt and/or solvate equivalent per day.

In one embodiment, a therapeutically effective amount of the compound, composition, pharmaceutical composition or medicament of the invention is administered at least once a day, twice a day, or at least three times a day.

In one embodiment, the compound, composition, pharmaceutical composition or medicament of the invention is administered twice a day, at a dosage ranging from about 10 mg to about 50 mg each dose, preferably from about 20 mg to about 40 mg each dose, more preferably at about 30 mg of free-base equivalent each dose. In one embodiment, each dose may correspond to one or more (in particular 2, 3, 4 or 5) unit forms, such as, for example, one or more oral unit form.

In one embodiment, the compound, composition, pharmaceutical composition or medicament of the invention is administered twice a day, at a total daily dosage ranging from about 20 mg to about 100 mg, preferably from about 40 mg to about 80 mg, more preferably at about 60 mg of free-base equivalent. In one embodiment, each dose may correspond to one or more (in particular 2, 3, 4 or 5) unit forms, such as, for example, one or more oral unit form.

In one embodiment, the compound, composition, pharmaceutical composition or medicament of the invention is administered once a day, at a dosage ranging from about 20 mg to about 100 mg, preferably from about 40 mg to about 80 mg, more preferably at about 60 mg of free-base equivalent.

In another embodiment, a therapeutically effective amount of the compound, composition, pharmaceutical composition, or medicament of the invention is administered every two, three, four, five, or six days.

In another embodiment, a therapeutically effective amount of the compound, composition, pharmaceutical composition, or medicament of the invention is administered twice a week, once a week, every two weeks, or once a month.

In another embodiment, a therapeutically effective amount of the compound, composition, pharmaceutical composition or medicament of the invention is administered for a period of time decided by the attending physician within the scope of sound medical judgment or for the rest of the life of the subject.

In another embodiment, a therapeutically effective amount of the compound, composition, pharmaceutical composition or medicament of the invention is administered once, twice, three times, four times, five times, six times, seven times, eight times, nine times, ten times, eleven times, twelve times, thirteen times, fourteen times, fifteen times, sixteen times, seventeen times, eighteen times, nineteen times, twenty times, twenty-one times, twenty-two times, twenty-three times, twenty-four times, twenty-five times, twenty-six times, twenty-seven times, twenty-eight times, twenty-nine times, thirty times or more.

In another embodiment, a therapeutically effective amount of the compound, composition, pharmaceutical composition or medicament of the invention is administered for a week, 2 weeks, 3 weeks, a month, two month, three month, or for the rest of the life of the subject.

In another embodiment, a therapeutically effective amount of the compound, composition, pharmaceutical composition or medicament of the invention is administered every month for a period at least 2; 3; 4; 5; 6 months or for the rest of the life of the subject.

In one embodiment, when the subject is/was diagnosed with sensorineural hearing loss, preferably with sudden sensorineural hearing loss, a therapeutically effective amount of the compound, composition, pharmaceutical composition, or medicament of the invention is administered for a period at least 2, 3, 4, 5 weeks or more, preferably for a period of at least 3, 4 or 5 weeks, more preferably for a period of 4 weeks after the appearance of symptoms or after the initial stages of case management. In one embodiment, when the subject is/was diagnosed with sensorineural hearing loss, preferably with sudden sensorineural hearing loss, a therapeutically effective amount of the compound, composition, pharmaceutical composition, or medicament of the invention is administered for a period at least 21, 22, 23, 24, 25, 26, 27, 28, 29, 30, 31, 32, 33, 34, 35 days or more, preferably for a period of at least 25, 26, 27, 28, 29, 30 or 31 days, more preferably for a period of 28 days after the appearance of symptoms or after the initial stages of case management.

In one embodiment, the subject receives the first administration of the compound, composition, pharmaceutical composition, or medicament of the invention at most one week, preferably at most 6, 5, 4, 3, 2 or 1 day after the appearance of symptoms, including, without limitation, hearing loss or tinnitus.

In one embodiment, when the subject is/was diagnosed with cancer, a therapeutically effective amount of the compound, composition, pharmaceutical composition, or medicament of the invention is administered before, during and/or after chemotherapy, preferably platinum-based chemotherapy, more preferably cisplatin-, carboplatin- or oxaliplatin-based chemotherapy or a combination thereof.

In one embodiment, a therapeutically effective amount of the compound, composition, pharmaceutical composition, or medicament of the invention is administered before platinum-based chemotherapy, preferably cisplatin-, carboplatin- or oxaliplatin-based chemotherapy or a combination thereof, such as for 1 day, 2 days, 3 days, 4 days, 5 days, 6 days, 7 days or more before.

In one embodiment, a therapeutically effective amount of the compound, composition, pharmaceutical composition, or medicament of the invention is administered after platinum-based chemotherapy, preferably cisplatin-, carboplatin- or oxaliplatin-based chemotherapy or a combination thereof, such as for 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days or more after.

In one embodiment, a therapeutically effective amount of the compound, composition, pharmaceutical composition, or medicament of the invention is administered immediately before and/or immediately after platinum-based chemotherapy, preferably cisplatin-, carboplatin- or oxaliplatin-based chemotherapy or a combination thereof.

In one embodiment, a therapeutically effective amount of the compound, composition, pharmaceutical composition, or medicament of the invention is administered for one day, two days, three days, four days or more before and for 1 day, two days, three days, four days, five days, six days, a week, two weeks, three weeks or more after platinum-based chemotherapy, preferably cisplatin-, carboplatin- or oxaliplatin-based chemotherapy or a combination thereof. In one embodiment, a therapeutically effective amount of the compound, composition, pharmaceutical composition, or medicament of the invention is administered for at least one day before and for at least 14 days after platinum-based chemotherapy. In one embodiment, a therapeutically effective amount of the compound, composition, pharmaceutical composition, or medicament of the invention is administered for one day before and for 14 days after platinum-based chemotherapy.

In one embodiment, a therapeutically effective amount of the compound, composition, pharmaceutical composition, or medicament of the invention is administered at each cycle of platinum-based chemotherapy, such as, for example, at each of 1, 2, 3, 4, 5, 6, 7, 8, 9, 10 or more cycles of platinum-based chemotherapy, preferably at each of 6 cycles of platinum-based chemotherapy.

In one embodiment, the compound, composition, pharmaceutical composition or medicament of the invention is to be administered systemically or locally.

In one embodiment, the compound, composition, pharmaceutical composition or medicament of the invention is to be administered by injection, orally, topically, nasally, by inhalation, buccally, rectally, intratracheally, transmucosally, transtympanically, by percutaneous administration, intramuscularly or by parenteral administration.

In one embodiment, the compound, composition, pharmaceutical composition or medicament of the invention is to be administered by injection, preferably is to be systemically injected. Examples of formulations adapted to systemic injections include, but are not limited to: liquid solutions or suspensions, solid forms suitable for solution in, or suspension in, liquid prior to injection. Examples of systemic injections include, but are not limited to, intravenous, subcutaneous, intramuscular, intradermal, intravitreal, and intraperitoneal injection, or perfusion. In another embodiment, when injected, the compound, composition, pharmaceutical composition or medicament of the invention is sterile. Methods for obtaining a sterile pharmaceutical composition include, without limitation, sterile filtration, terminal sterilization (dry heat, radiation, moist heat, gases, gamma radiation) or sterilization via aseptic processing.

In one embodiment, the compound, composition, pharmaceutical composition or medicament of the invention is to be systemically administered, preferably is to be orally administered. Examples of formulations adapted to oral administration include, but are not limited to: solid forms, liquid forms and gels. Examples of solid forms adapted to oral administration include, but are not limited to, pill, tablet, capsule, soft gelatine capsule, hard gelatine capsule, caplet, compressed tablet, cachet, wafer, sugar-coated pill, sugar coated tablet, or dispersing and/or disintegrating tablet, powder, solid forms suitable for solution in, or suspension in, liquid prior to oral administration and effervescent tablet. Examples of liquid forms adapted to oral administration include, but are not limited to, solutions, suspensions, drinkable solutions, elixirs, sealed phial, portion, drench, syrup and liquor.

In another embodiment, the compound, composition, pharmaceutical composition or medicament of the invention is to be topically administered. Examples of formulations adapted to topical administration include, but are not limited to, sticks, waxes, creams, lotions, ointments, balms, gels, masks, leave-on washes and/or the like.

In one embodiment, the compound, composition, pharmaceutical composition or medicament of the invention is to be administered directly in the ear, in particular, in the inner ear, in the middle ear, in the external ear, in the cochlea, or in the vestibule by transtympanic or intratympanic administration. This administration route may be preferred for introducing a direct and long term effect on the ear. Said administration can be accomplished topically or by injection. Delivery techniques for such administration may include the use of devices or drug carriers to transport and/or deliver the active principle to the ear, where it diffuses into the ear, is actively infused or is injected. Examples of formulations adapted to such administration include, but are not limited to, otowicks, round window catheters, various types of gels, foams, fibrins, emulsions, solutions, patches or other drug carriers, which are placed in the ear, and loaded with the composition of the invention for sustained release. It may also include devices that are inserted into the cochlear duct or any other part of the cochlea.

The diffusion of the composition across middle-inner ear interface tissue structures, in particular the round window membrane, depends on a variety of factors, such as molecular weight, concentration, liposolubility, electrical charge, and thickness of the membrane (Goycoolea M. and Lundman L., Microscopy Research and Technique 36: 201-211 (1997).

In one embodiment, the compound described here above is to be administered in a immediate-release form.

In one embodiment, the compound described here above is to be administered in a sustained-release form. In another embodiment, the composition, the pharmaceutical composition or the medicament of the invention comprises a delivery system that controls the release of the at least one compound of Formula I, preferably of (+)-azasetron or a pharmaceutically acceptable salt and/or solvate thereof, more preferably of (+)-azasetron besylate, (+)-azasetron hydrochloride, (+)-azasetron malate or a mixture thereof.

In another embodiment, the composition, pharmaceutical composition or medicament of the invention comprises sustained-release drug delivery agents, such as biodegradable polymers. As used herein, a sustained-release drug delivery agent is a composition, e.g., a polymeric matrix, which provides a reservoir or vehicle for release of a therapeutic agent over an extended time in a subject, e.g., in a subject's ear canal.

In some embodiments, a sustained-release drug delivery agent is a material, such as, for example, a polyelectrolyte or thermo-responsive polymer, that undergoes a viscosity increase after being administered to a subject, e.g., administered into a subject's ear canal.

It should be appreciated that the sustained-release drug delivery agents include a variety of materials, including, without limitation, polymeric materials that form in response to temperature change (e.g., poloxamers), polyelectrolyte complexing (e.g., chitosanlchondroitin sulfate), polymer cross-linking (both physical and chemical, e.g., with rheological synergism or hyaluronic acid derivatives, respectively), or sensitivity to photo or electromagnetic waves (e.g., UV or microwaves), solvent exchange, or pH. In certain embodiments, the sustained-release drug delivery agent is a hydrophilic material.

In some embodiments, the sustained-release drug delivery agent is a matrix-forming agent. Matrix-forming agents are generally liquid at ambient conditions, however, once administered to a subject, the matrix forming agent gels (i.e., becomes more viscous). In various aspects, for example, the matrix-forming agent changes viscosity once administered into a patient's ear canal forming in situ a reservoir in contact with or nearby the tympanic membrane. A reservoir in contact with the tympanic membrane maximizes exposure and concentration of the therapeutic agent at the surface of the tympanic membrane, thus increasing flux of the agent across the tympanic membrane and into the middle and/or inner ear. Exemplary matrix-forming agents include, but are not limited to, polyelectrolyte complexes (e.g., chitosan-chondroitin complexes), thermo-responsive gelling agents (e.g., poloxamers), pre-polymers, alginates, un-crosslinked polymers, and monomers.

In the compositions of the present invention, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, gingival or mucosal or mucoadhesive formulations, aerosols, sprays, transtympanical, implants, subcutaneous, transdermal, topical, intraperitoneal, intramuscular, intravenous, subdermal, transdermal, intrathecal and intranasal administration forms and rectal administration forms.

In one embodiment, the active principle, alone or in combination with another active principle, can be administered in an oral-route form (immediate or sustained-released), preferably as tablets.

In one embodiment, a tablet for oral-route administration comprises or consists of or consists essentially of at least one compound of Formula I or a pharmaceutically acceptable salt and/or solvate thereof, preferably (+)-azasetron or a pharmaceutically acceptable salt and/or solvate thereof, more preferably (+)-azasetron besylate, (+)-azasetron hydrochloride, (+)-azasetron malate or a mixture thereof.

In one embodiment, the compound of Formula I or a pharmaceutically acceptable salt and/or solvate thereof, preferably (+)-azasetron or a pharmaceutically acceptable salt and/or solvate thereof, more preferably (+)-azasetron besylate, (+)-azasetron hydrochloride, (+)-azasetron malate or a mixture thereof may be formulated within a tablet for oral-route administration comprising or consisting of about 0.1 to 10000 milligrams, preferably from about 0.1 to 1000 milligrams, more preferably from about 0.1 to 100 milligrams, even more preferably from about 1 to 100 milligrams per dose or so.

In one embodiment, a tablet for oral-route administration comprises or consists of at least about 0.01 mg, 0.05 mg, 0.1 mg, 0.2 mg, 0.3 mg, 0.4 mg, 0.5 mg, 0.6 mg, 0.7 mg, 0.8 mg, 0.9 mg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 20 mg, 25 mg, 30 mg, 35 mg, 40 mg, 45 mg, 50 mg, 75 mg, 100 mg, 125 mg, 150 mg, 175 mg, 200 mg or more of compound of Formula I or a pharmaceutically acceptable salt and/or solvate thereof, preferably (+)-azasetron or a pharmaceutically acceptable salt and/or solvate thereof, more preferably (+)-azasetron besylate, (+)-azasetron hydrochloride, (+)-azasetron malate or a mixture thereof. In one embodiment, quantities of Formula (I) compound, preferably of (+)-azasetron, are expressed as free-base equivalent. Therefore, in one embodiment, a tablet for oral-route administration comprises or consists of at least about 0.01 mg, 0.05 mg, 0.1 mg, 0.2 mg, 0.3 mg, 0.4 mg, 0.5 mg, 0.6 mg, 0.7 mg, 0.8 mg, 0.9 mg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 20 mg, 25 mg, 30 mg, 35 mg, 40 mg, 45 mg, 50 mg, 75 mg, 100 mg, 125 mg, 150 mg, 175 mg, 200 mg or more of the free-base compound of Formula (I), preferably of free-base (+)-azasetron. In one embodiment, quantities of Formula (I) compound, preferably of (+)-azasetron, are expressed as salt and/or solvate equivalent. Therefore, in one embodiment, a tablet for oral-route administration comprises or consists of at least about 0.01 mg, 0.05 mg, 0.1 mg, 0.2 mg, 0.3 mg, 0.4 mg, 0.5 mg, 0.6 mg, 0.7 mg, 0.8 mg, 0.9 mg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 20 mg, 25 mg, 30 mg, 35 mg, 40 mg, 45 mg, 50 mg, 75 mg, 100 mg, 125 mg, 150 mg, 175 mg, 200 mg or more of a pharmaceutically acceptable salt and/or solvate of the compound of Formula (I), preferably of a pharmaceutically acceptable salt and/or solvate of (+)-azasetron, preferably (+)-azasetron besylate, (+)-azasetron hydrochloride or (+)-azasetron malate.

In one embodiment, a tablet for oral-route administration may comprises one or more disintegrants, one or more binders, one or more lubricants and/or one or more coatings.

In one embodiment, a tablet for oral-route administration comprises at least one disintegrant. Examples of disintegrants include, but are not limited to, microcrystalline cellulose (MCC), carboxymethylstarch-sodium (such as Pirimojel and Explotab), carboxymethylcellulose calcium (CMC-Ca), carboxymethylcellulose sodium (CMC-Na), crosslinked CMC (such as Ac-Di-Sol), crosslinked PVP (such as Crospovidone, Polyplasdone or Kollidon XL), alginic acid, sodium alginate, guar gum.

In one embodiment, a tablet for oral-route administration comprises at least one binder. Examples of binders include, but are not limited to, starch, polyvinylpyrrolidone (PVP), hydroxypropylmethylcellulose (HPMC) and polyethylene glycols (PEG).

In one embodiment, a tablet for oral-route administration comprises at least one lubricant. Examples of lubricant include, but are not limited to, magnesium stearate, aluminum stearate, calcium stearate, polyethylene glycol (PEG) 4000 to 8000, talc, hydrogenated castor oil, stearic acid and salts thereof, glycerol esters, Na-stearylfumarate, hydrogenated cotton seed oil and the like.

In one embodiment, a tablet for oral-route administration comprises at least one coating. Examples of coatings include, but are not limited to, hydroxypropylmethylcellulose (HPMC), polyethylene glycol (PEG), polysorbate 80, polyvinylpyrrolidone (PVP), PVP-vinyl acetate copolymer (PVP-VA), polyvinyl alcohol (PVA), and sugar. Further coatings comprise pigments, dies, lakes, titanium dioxide, iron oxides, anti-tacking agents (such as talk and softeners like PEG 3350, 4000, 6000, 8000) or others.

In one embodiment, a tablet for oral-route administration is an immediate release tablet. In one embodiment, a tablet for oral-route administration is an orodispersible tablet. In one embodiment, a tablet for oral-route administration is a sustained-release tablet.

The composition, pharmaceutical composition or medicament of the invention may contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions or lyophilisates which upon addition, depending on the case, of sterilized water or physiological saline, permit the constitution of injectable solutions.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy administration via syringe or needle is obtained. It must be stable under the conditions of manufacture and storage and must be preserved against the contaminating action of microorganisms, such as bacteria and fungi.

Solutions comprising at least one compound of the invention as free-base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations may contain a preservative to prevent the growth of microorganisms.

The compounds of the invention can be formulated into a composition in a neutral or salt form. Pharmaceutically acceptable salts include the acid addition salts which are formed with inorganic acids such as, for example, hydrochloric or phosphoric acids, or such organic acids as acetic, benzenesulfonic, malic, oxalic, tartaric, mandelic, and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions may be prepared by incorporating the compound of the invention in the required amount in the appropriate solvent with one or several of the other ingredients enumerated above, as required, followed by sterile filtration or other processing technique capable of rendering the solution sterile. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are formulation of the bulk solution, followed by sterile filtration and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. The liquid compositions may include aqueous solutions with and without organic co-solvents, aqueous or oil suspensions, emulsions with edible oils, liposomes or nano-emulsion as well as similar pharmaceutical vehicles. These particular aqueous solutions are especially suitable for transtympanic, intravenous, intramuscular, subcutaneous and intraperitoneal administration. Advantageously the viscosity of the formulation for transtympanic solution is between 5000 and 25000 mPas (milliPascal second), preferably between 15000 and 20000 mPas, so that a longer period of administration of the active principle into the inner ear is achieved. In this connection, sterile aqueous media which can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion. Some variation in dosage, pH (preferably between about 5 and 9), and formulation will necessarily occur depending on the condition of the subject being treated, the routes of administration, the compound used.

The person responsible for administration will, in any event, determine the appropriate dose for the individual subject. The compounds of the invention may be formulated within a therapeutic mixture to comprise about 0.1 to 10000 milligrams, preferably from about 0.2 to 1000 milligrams, more preferably from about 0.3 to 100 milligrams per dose or so. Multiple doses can also be administered.

Another object of the invention is a method for treating an ear disease, disorder or condition in a subject in need thereof, comprising or consisting of administering to the subject a therapeutically effective amount of at least one compound of Formula I or a pharmaceutically acceptable salt and/or solvate thereof.

In one embodiment, the method of the invention is for preventing an ear disease, disorder or condition. In another embodiment, the method of the invention is for alleviating a symptom of an ear disease, disorder or condition or for curing an ear disease, disorder or condition.

In one embodiment, the method comprises or consists of administering to the subject a therapeutically effective amount of free-base (+)-azasetron or a pharmaceutically acceptable salt and/or solvate thereof (in particular, (+)-azasetron besylate, (+)-azasetron hydrochloride, (+)-azasetron malate or a mixture thereof).

Another object of the invention is a method for treating hearing loss, preferably sensorineural hearing loss in a subject in need thereof, comprising or consisting of administering to the subject a therapeutically effective amount of at least one compound of Formula I or a pharmaceutically acceptable salt and/or solvate thereof.

In one embodiment, the method of the invention is for preventing hearing loss, preferably sensorineural hearing loss. In another embodiment, the method of the invention is for alleviating a symptom of hearing loss, preferably of sensorineural hearing loss or for curing hearing loss, preferably sensorineural hearing loss.

In one embodiment, the method comprises or consists of administering to the subject a therapeutically effective amount of free-base (+)-azasetron or a pharmaceutically acceptable salt and/or solvate thereof (in particular, (+)-azasetron besylate, (+)-azasetron hydrochloride, (+)-azasetron malate or a mixture thereof).

Another object of the invention is a method for treating ototoxic compound-induced hearing loss, preferably platinum-induced hearing loss in a subject in need thereof, comprising or consisting of administering to the subject a therapeutically effective amount of at least one compound of Formula I or a pharmaceutically acceptable salt and/or solvate thereof.

In one embodiment, the method of the invention is for preventing ototoxic compound-induced hearing loss, preferably platinum-induced hearing loss. In another embodiment, the method of the invention is for alleviating a symptom of ototoxic compound-induced hearing loss, preferably of platinum-induced hearing loss or for curing ototoxic compound-induced hearing loss, preferably platinum-induced hearing loss.

In one embodiment, the method comprises or consists of administering to the subject a therapeutically effective amount of free-base (+)-azasetron or a pharmaceutically acceptable salt and/or solvate thereof (in particular, (+)-azasetron besylate, (+)-azasetron hydrochloride, (+)-azasetron malate or a mixture thereof).

Another object of the invention is a method for treating cisplatin-induced hearing loss in a subject in need thereof, comprising or consisting of administering to the subject a therapeutically effective amount of at least one compound of Formula I or a pharmaceutically acceptable salt and/or solvate thereof.

In one embodiment, the method of the invention is for preventing cisplatin-induced hearing loss. In another embodiment, the method of the invention is for alleviating a symptom of cisplatin-induced hearing loss or for curing cisplatin-induced hearing loss.

In one embodiment, the method comprises or consists of administering to the subject a therapeutically effective amount of free-base (+)-azasetron or a pharmaceutically acceptable salt and/or solvate thereof (in particular, (+)-azasetron besylate, (+)-azasetron hydrochloride, (+)-azasetron malate or a mixture thereof).

Another object of the invention is a method for restoring vestibular functionality in a subject in need thereof, preferably in a subject affected with a lesional vestibular disease, comprising or consisting of administering to the subject a therapeutically effective amount of at least one compound of Formula I or a pharmaceutically acceptable salt and/or solvate thereof.

In one embodiment, the method of the invention is for preventing a lesional vestibular disease. In another embodiment, the method of the invention is for alleviating a symptom of a lesional vestibular disease or for curing a lesional vestibular disease.

In one embodiment, the method comprises or consists of administering to the subject a therapeutically effective amount of free-base (+)-azasetron or a pharmaceutically acceptable salt and/or solvate thereof (in particular, (+)-azasetron besylate, (+)-azasetron hydrochloride, (+)-azasetron malate or a mixture thereof).

Another object of the invention is a method for restoring hearing and/or balance in a subject in need thereof, comprising or consisting of administering to the subject a therapeutically effective amount of at least one compound of Formula I or a pharmaceutically acceptable salt and/or solvate thereof.

In one embodiment, the method comprises or consists of administering to the subject a therapeutically effective amount of free-base (+)-azasetron or a pharmaceutically acceptable salt and/or solvate thereof (in particular, (+)-azasetron besylate, (+)-azasetron hydrochloride, (+)-azasetron malate or a mixture thereof).

Another object of the invention is a method for reducing loss of hair cells in the inner ear of a subject in need thereof, comprising or consisting of administering to the subject a therapeutically effective amount of at least one compound of Formula I or a pharmaceutically acceptable salt and/or solvate thereof.

In one embodiment, the method of the invention is for preventing the loss of hair cells in the inner ear. In another embodiment, the method of the invention is for alleviating a symptom of the loss of hair cells in the inner ear or for curing the loss of hair cells in the inner ear.

In one embodiment, the method comprises or consists of administering to the subject a therapeutically effective amount of free-base (+)-azasetron or a pharmaceutically acceptable salt and/or solvate thereof (in particular, (+)-azasetron besylate, (+)-azasetron hydrochloride, (+)-azasetron malate or a mixture thereof).

Another object of the invention is a method for reducing loss of synapses between hair cells and neurons in the inner ear of a subject in need thereof, comprising or consisting of administering to the subject a therapeutically effective amount of at least one compound of formula I or a pharmaceutically acceptable salt and/or solvate thereof.

In one embodiment, the method of the invention is for preventing the loss of synapses between hair cells and neurons in the inner ear. In another embodiment, the method of the invention is for alleviating a symptom of the loss of synapses between hair cells and neurons in the inner ear or for curing the loss of synapses between hair cells and neurons in the inner ear.

In one embodiment, the method comprises or consists of administering to the subject a therapeutically effective amount of free-base (+)-azasetron or a pharmaceutically acceptable salt and/or solvate thereof (in particular, (+)-azasetron besylate, (+)-azasetron hydrochloride, (+)-azasetron malate or a mixture thereof).

Another object of the invention is a method for reducing loss of neurons in the inner ear of a subject in need thereof, comprising or consisting of administering to the subject a therapeutically effective amount of at least one compound of Formula I or a pharmaceutically acceptable salt and/or solvate thereof.

In one embodiment, the method of the invention is for preventing the loss of neurons in the inner ear. In another embodiment, the method of the invention is for alleviating a symptom of the loss of neurons in the inner ear or for curing the loss of neurons in the inner ear.

In one embodiment, the method comprises or consists of administering to the subject a therapeutically effective amount of free-base (+)-azasetron or a pharmaceutically acceptable salt and/or solvate thereof (in particular, (+)-azasetron besylate, (+)-azasetron hydrochloride, (+)-azasetron malate or a mixture thereof).

Another object of the invention is a method for reducing loss of supporting cells in the inner ear of a subject in need thereof, comprising or consisting of administering to the subject a therapeutically effective amount of at least one compound of Formula I or a pharmaceutically acceptable salt and/or solvate thereof.

In one embodiment, the method of the invention is for preventing the loss of supporting cells in the inner ear. In another embodiment, the method of the invention is for alleviating a symptom of the loss of supporting cells in the inner ear or for curing the loss of supporting cells in the inner ear.

In one embodiment, the method comprises or consists of administering to the subject a therapeutically effective amount of free-base (+)-azasetron or a pharmaceutically acceptable salt and/or solvate thereof (in particular, (+)-azasetron besylate, (+)-azasetron hydrochloride, (+)-azasetron malate or a mixture thereof).

In one embodiment, the loss of hair cells, synapses, neurons or supporting cells may be induced by an acoustic trauma, such as, for example, loud noise exposure, chronic noise exposure, aging, illnesses (including but not limited to high blood pressure and diabetes), ototoxic drugs, head trauma, tumors, blast exposure, autoimmune inner ear disease, idiopathic causes, viral or bacterial infections.

Another object of the invention is a method for inhibiting inflammation in the ear (including, without limitation, inflammation in the inner ear, middle ear, cochlea and/or vestibule) of a subject in need thereof, comprising or consisting of administering to the subject a therapeutically effective amount of at least one compound of Formula I or a pharmaceutically acceptable salt and/or solvate thereof.

In one embodiment, the method of the invention is for preventing inflammation in the ear (including, without limitation, inflammation in the inner ear, middle ear, cochlea and/or vestibule). In another embodiment, the method of the invention is for alleviating a symptom of inflammation in the ear (including, without limitation, inflammation in the inner ear, middle ear, cochlea and/or vestibule) or for curing inflammation in the ear (including, without limitation, inflammation in the inner ear, middle ear, cochlea and/or vestibule).

In one embodiment, the method comprises or consists of administering to the subject a therapeutically effective amount of free-base (+)-azasetron or a pharmaceutically acceptable salt and/or solvate thereof (in particular, (+)-azasetron besylate, (+)-azasetron hydrochloride, (+)-azasetron malate or a mixture thereof).

Preferably, the methods of the invention comprise or consist of administering (+)-azasetron besylate, (+)-azasetron hydrochloride or (+)-azasetron malate to the subject.

EXAMPLES

Figure 1:
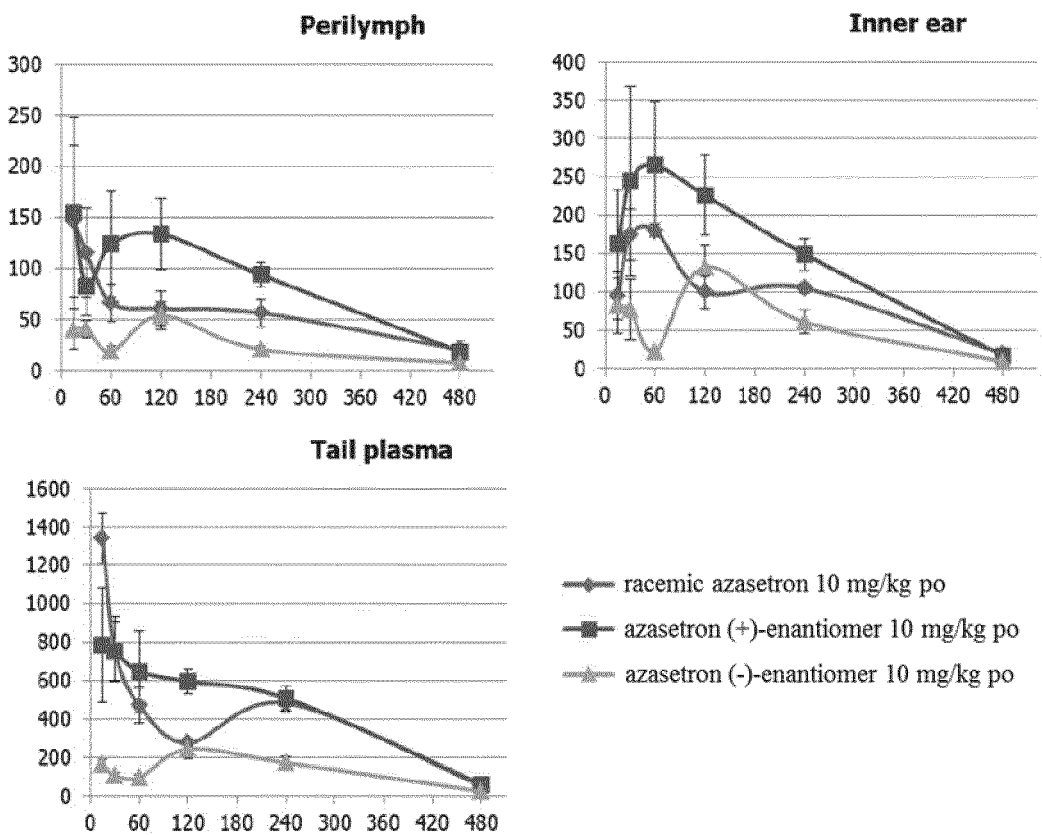
FIG. 1 is a set of three graphs comparing the concentration (nM) of the racemic and two enantiomers of azasetron in the perilymph, the inner ear, and the peripheral plasma (tail plasma) after oral administration, at termination time-point. Average per time-point subgroups within treatment groups (+/−SE).

The present invention is further illustrated by the following examples.

Example 1: Pharmacokinetics Study

Material and Methods
Test Animals Assignment to the Study

The 72 male Wistar rats received on 28 Jan. 2016 from Janvier (Janvier, Le Genest-St-Isle) were assigned to the study. They were divided in 3 groups of 24 animals each, one group per test article. Each group was divided in 7 sub-groups according to the 6-termination time-points.

72 Wistar rats were subjected to oral single dose administration of the test article, racemic azasetron hydrochloride, azasetron hydrochloride (+) or azasetron hydrochloride (−), and sacrificed at different time-points to assess the exposure of the test article in the inner ear, perilymph, and plasma.

Group racemic azasetron: 24 male Wistar, 4 rats per time-point: 10 mg/kg azasetron HCl dissolved in NaCl 0.9%. Administrated as 5 mL/kg p.o.;

Group azasetron (+): 24 male Wistar, 4 rats per time-point: 10 mg/kg (+)-azasetron HCl dissolved in NaCl 0.9%. Administrated as 5 mL/kg p.o.;

Group azasetron (−): 24 male Wistar, 4 rats per time-point: 10 mg/kg (−)-azasetron HCl dissolved in NaCl 0.9%. Administrated as 5 mL/kg p.o.

There were 6 termination time-points for each test article. At time-points 15/30/60/120/240/480 minutes after administration: peripheral plasma from the tail was sampled. The animals were sacrificed by i.v. administration of 0.25 mL/rat of a 160 mg/mL pentobarbital solution. Following sacrifice, the heart blood and both tympanic bullas (left and right) were sampled.

Sample Preparation for Bio-Analytics
Perilymph and Inner Ear Samples

Both tympanic bullas (left and right) were collected, however, only the left one was used for the perilymph and inner ear analysis. The right bulla was stored at −20° C. for future needs when required. For animal IDs 1 and 4, the right bulla was used for the sampling of perilymph and inner ear.

The left bulla was dissected fresh. Briefly, the bulla was opened via the auditory opening to reveal the bone surrounding the cochlea after which the tip of the bone was removed with forceps and a 10 µL pipette tip was inserted to withdraw perilymph.

Upon exposure of the tip of the cochlea, 2 µL of perilymph (fluid) could be recovered from the bulla. The perilymph was brought to 10 µL by the addition of 8 µL water, and then extract via the addition of 30 µL of acetonitrile. After that, the samples were centrifuged and the supernatant was transferred to a glass vial appropriate for the HPLC-MS auto-sampler.

Following recovering of the perilymph, the bones of the inner ear and cochlea components were removed with fine forceps and added to a tared Eppendorf tube. The collection was weighed and brought to 10 mg with the addition of water and placed on ice until extraction. 30 µL of acetonitrile was added and the tubes were incubated in an ultrasound bath, after which they were centrifuged and the supernatant was transferred to a glass vial appropriate for the HPLC-MS auto-sampler. In the process or removing the bones of the inner ear, they were finely distributed in the media and broken by forceps. (Due to the very low volume of the tissue and its fine structure, separate grinding is considered risky vs the potential losses to plastic and media. The materials are very fine in nature and the bone particles are small thus providing only short interfaces to media. The absence of fat and the incubation in solvent is intended to provide sufficient solubility of active ingredient).

The acetonitrile used in the sample preparation for bio-analysis contained the internal standard for the HPLC-MS analysis.

Tail Plasma

30 µL acetonitrile including the internal standard were added to each 10 µL plasma sample. After adding the acetonitrile, the samples were mixed by vortex and further centrifuged. The supernatant was transferred to a glass vial appropriate for the HPLC-MS auto-sampler.

Heart Plasma

The plasma samples from the heart blood are stored at −20° C. for future optional analysis when needed.

LC-MS/MS Apparatus

The LC system comprised an Agilent 1260 liquid chromatography equipped with a binary pump and a column oven, together with a PAL HTS-xt auto-sampler. It is linked to the AB SCIEX TRIPLE QUADTM 4500 (triple-quadrupole) instrument with an ESI interface and a switching valve integrated (Mass spectrometric analysis). The data acquisition and control system were created using Analyst Software from Applied Biosystems Inc.

The test article, azasetron hydrochloride, used for the standard curve was provided by the Sponsor. Water and acetonitrile were HPLC grade. All other solvents and chemicals were analytical grade or better.

Results
Plasma Kinetic and Distribution to Inner Ear of Azasetron Following a Single Oral Dose of Racemic Azasetron, (+)-Azasetron Hydrochloride and (−)-Azasetron Hydrochloride in Wistar Rats This study was conducted to compare exposure to azasetron following administration of a single oral dose (10 mg/kg) of racemic azasetron hydrochloride, (+)-azasetron hydrochloride and (−)-azasetron hydrochloride. The concentration of the test articles in the inner ear samples were analyzed by HPLC-MS and quantified by comparison with a known concentration standard curve (Table 1).

TABLE 1

Concentration (ng azasetron free-base/g tissue) of racemic azasetron, (+)-azasetron and (−)-azasetron in the inner ear tissue at termination time-point. Average per time-point subgroups within treatment groups, and standard error (SE).

| Treatment | Dose (mg/kg) | Route | Time | Average Inner ear (ng/g) | SE Inner ear (ng/g) |
|---|---|---|---|---|---|
| Racemic azasetron | 10 | p.o. | 15 | 25 | 13 |
| | | | 30 | 61 | 13 |
| | | | 60 | 63 | 3 |
| | | | 120 | 35 | 9 |
| | | | 240 | 37 | 2 |
| | | | 480 | 7 | 2 |
| (+)-azasetron | 10 | p.o. | 15 | 57 | 29 |
| | | | 30 | 86 | 50 |
| | | | 60 | 93 | 34 |
| | | | 120 | 79 | 21 |
| | | | 240 | 52 | 8 |
| | | | 480 | 6 | 0 |
| (−)-azasetron | 10 | p.o. | 15 | 29 | 15 |
| | | | 30 | 27 | 16 |
| | | | 60 | 8 | 1 |
| | | | 120 | 46 | 11 |
| | | | 240 | 21 | 6 |
| | | | 480 | 3 | 1 |

The concentration of the racemic and two enantiomers of azasetron hydrochloride in the perilymph, the inner ear and the peripheral plasma is represented in FIG. 1 and Table 2.

TABLE 2

(AUC) Area under the curve (nM min) of the azasetron free-base pharmacokinetics.

| Treatment | Dose (mg/kg) | Route | Time | Perilymph AUC nM min | Inner ear AUC nM min | Tail plasma AUC nM min |
|---|---|---|---|---|---|---|
| Racemic azasetron | 10 | p.o | 15 | 1099 | 712 | 10078 |
| | | | 30 | 1965 | 2019 | 15807 |
| | | | 60 | 2729 | 5319 | 18556 |
| | | | 120 | 3811 | 8394 | 22450 |
| | | | 240 | 7026 | 12260 | 45507 |
| | | | 480 | 9243 | 14889 | 64797 |
| | | Total AUC | | 25873 | 43592 | 177194 |
| (+)-azasetron | 10 | p.o | 15 | 1161 | 1225 | 5897 |
| | | | 30 | 1783 | 3059 | 11548 |
| | | | 60 | 3102 | 7643 | 21012 |
| | | | 120 | 7719 | 14739 | 37299 |
| | | | 240 | 13642 | 22527 | 66332 |
| | | | 480 | 13504 | 19844 | 68681 |
| | | Total AUC | | 40910 | 69036 | 210768 |
| (−)-azasetron | 10 | p.o | 15 | 304 | 614 | 1217 |
| | | | 30 | 613 | 1189 | 2037 |
| | | | 60 | 898 | 1484 | 3092 |
| | | | 120 | 2179 | 4631 | 10183 |
| | | | 240 | 4482 | 11560 | 24941 |
| | | | 480 | 3425 | 8351 | 23978 |
| | | Total AUC | | 11901 | 27829 | 65448 |

Following administration of a single equivalent oral dose of each compound, greater exposure (total AUC) to azasetron was observed in the perilymph, inner ear, and plasma after administration of (+)-azasetron than that observed after administration of racemic azasetron or (−)-azasetron.

Example 2: Activity of (+)-Azasetron Besylate on Noise-Induced Hearing Loss

Material and Methods

Animals

All experiments were performed using 7-week-old male Wistar rats (CERJ, Le Genest, France) in accordance with the French Ministry of Agriculture regulations and European Community Council Directive no. 86/609/EEC, OJL 358. The rats were fed a standard diet ad libitum and maintained on a 12 hours' light-dark cycle.

Audiometry

Auditory Brainstem Reponses (ABR) and Distortion Product Otoacoustic Emissions (DPOAE) were recording using a RZ6 Auditory Workstation (Tucker-Davis Technologies, Alachua, Fla., USA) with animals deeply anesthetized using 90 mg/kg ketamine and 10 mg/kg xylazine and placed on a 35° C. recirculating heating pad inside a sound attenuating cubicle (Med Associates Inc., St. Albans, Vt., USA) throughout the experiment.

For ABR recordings, three stainless steel needle electrodes were placed subdermally over the vertex, the right mastoid and right hind leg of each animal. Tone-pips (5 msec duration presented at a rate of 21/s) at 8, 16 and 24 kHz were delivered to the right ear using a calibrated MF-1 speaker in closed-field configuration (Tucker-Davis Technologies, Alachua, Fla., USA) at attenuating intensity until no reproducible response could be recorded. Close to the ABR threshold, the responses to 1000 acoustic stimuli in 5 dB steps were averaged. Responses were low-pass filtered at 3 kHz.

DPOAEs were recorded and using ER10B+ Low Noise DPOAE microphone (Etymotic Research, Inc., Elk Grove Village, Ill., USA) with acoustic stimuli delivered by two calibrated MF-1 speakers in closed-field configuration (Tucker-Davis Technologies, Alachua, Fla., USA). DPOAEs were recorded at fixed stimulus levels (L1=L2=70 dB SPL), with an f2/f1 ratio of 1.2. Responses were recorded at 4, 8, 16, 24 and 32 kHz.

Acoustic Trauma

Animals were exposed to 120 dB octave band noise (8-16 kHz) for 2 hours in groups of 4 rats, placed in individual compartments of a custom built circular cage placed on a 30-cm diameter platform rotating at 3 turns/minute (Aqila Innovation, Valbonne, France). The calibrated octave band noise generated by the RZ6 SigGen software was further amplified by a Crown D-75 amplifier in bridge mode (Crown Audio, Elkhart, Ind., USA) and delivered by four Beyma CPI6 compression tweeters (Acustica Beyma S. L., Moncada, Valencia, Spain) positioned 39 cm above the rotating platform, each 10 cm from the platform center.

Results

Comparative Effect of Intraperitoneal Administration of Racemic Azasetron, (+)-Azasetron and (−)-Azasetron on Ear Disorder The ability of the racemic and two enantiomers of azasetron hydrochloride to reduce SSNHL after acoustic trauma was evaluated in a randomized, vehicle-controlled study with 7 weeks old male Wistar rats. Rats were randomized to receive 4.22 mg/kg of the racemic, two enantiomers of azasetron or vehicle control (physiological saline) by intraperitoneal injection immediately after acoustic trauma, followed by daily dosing for a total of 14 days. Two days prior to acoustic trauma, baseline audiometric readings using auditory brainstem response (ABR) (8, 16, and 24 kHz) were recorded for each animal. Animals were exposed to 120-dB octave-band noise (8-16 kHz) for 2 hours to induce acoustic trauma.

Figure 2:
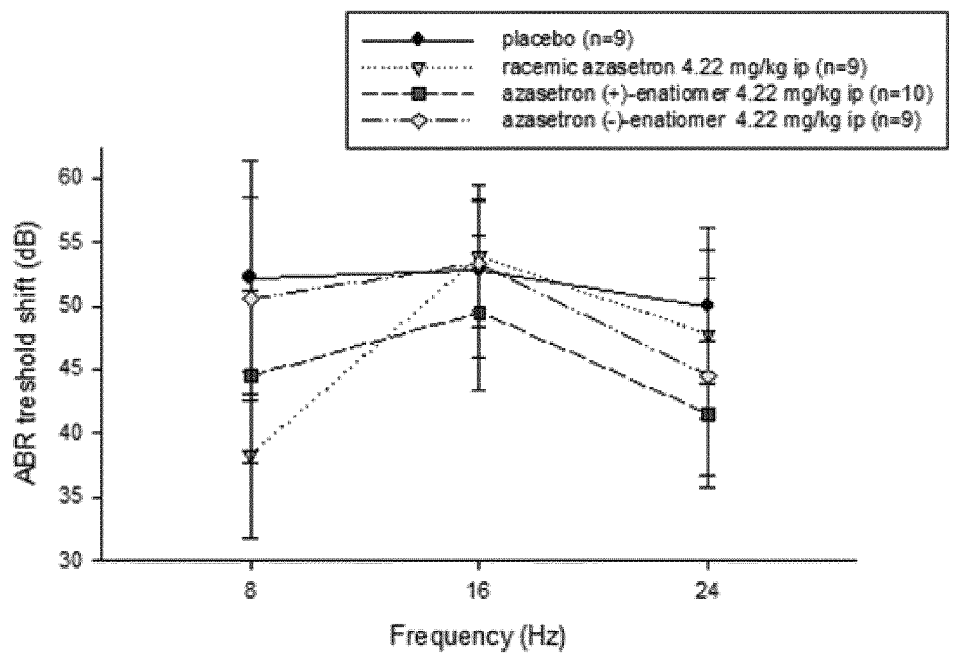
FIG. 2 is a graph comparing the effects of the racemic and two enantiomers of azasetron on auditory brainstem response (ABR) threshold shifts in a sensorineural hearing loss (SSNHL) model.

Results for auditory threshold shift are provided in FIG. 2.

Data show that the (+) enantiomer reduced ABR threshold shifts more than racemic azasetron or (−)-enantiomer across the tested frequencies when compared to the vehicle control group.

Protective Effect of Oral Administration of (+)-Azasetron Post-Trauma

The ability of the (+)-enantiomer of azasetron hydrochloride to reduce SSNHL after acoustic trauma was evaluated in a randomized, vehicle-controlled study in male Wistar rats, 7 weeks of age. Rats were randomized to receive 5, 10, or 20 mg/kg of the (+)-enantiomer of azasetron hydrochloride or vehicle control (physiological saline) by oral gavage immediately after acoustic trauma, followed by daily dosing for a total of 14 days. Two days prior to acoustic trauma, baseline audiometric readings using auditory brainstem response (ABR) (8, 16, and 24 kHz) and distortion-product otoacoustic emissions (DPOAE) (4, 8, 16, 24, and 32 kHz) were recorded for each animal. Post-trauma audiometry recordings were conducted at 14 days.

Figure 3:
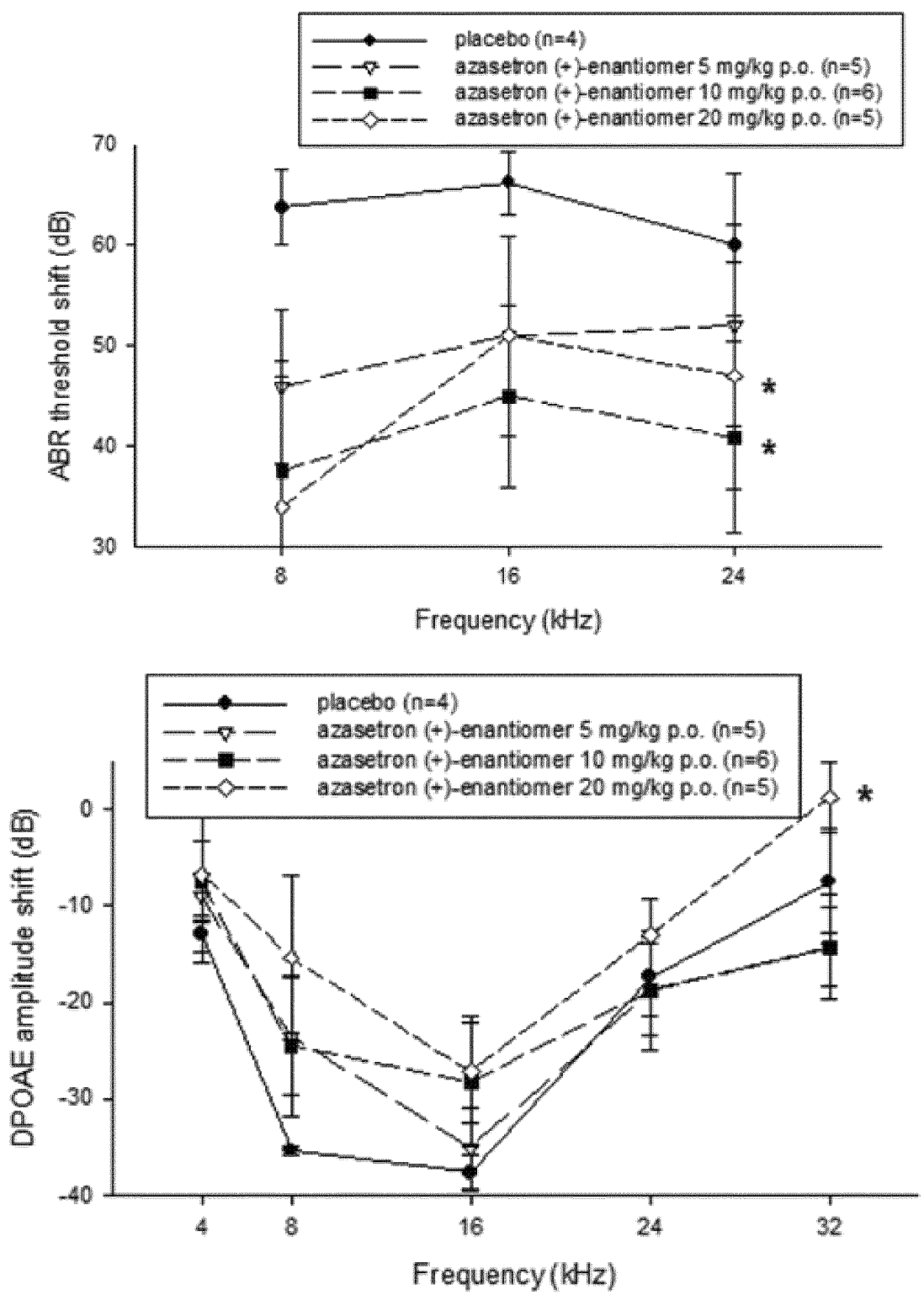
FIG. 3 is a set of two graphs showing the effect of the (+) enantiomer of azasetron at different doses on auditory brainstem response (ABR) threshold shifts and distortion product otoacoustic emission (DPOAE) amplitude loss in a SSNHL model. Statistical analyses were performed using 2-way analysis of variance (ANOVA) (treatment group, stimulus frequency) with Holm-Sidak post-test versus vehicle controls. A P value of ≤0.05 was statistically significant.

Results for auditory threshold shifts are provided in FIG. 3.

Data show that 10 and 20 mg/kg of the (+) enantiomer significantly reduced ABR threshold shifts by a mean of 35.1% and 30.5%, respectively, from baseline to day 14, indicating a mean 22.3 and 19.4 dB improvement in hearing, respectively. When compared to the vehicle control group, 10- and 20-mg/kg doses of the (+) enantiomer demonstrate a treatment effect that reduces the hearing loss (average) from moderately severe (56 to 70 dB) to mild/moderate (26 to 40 dB/41 to 55 dB) based on American Speech Language Hearing Association (ASLHA) criteria (ASLHA, 2015).

Otoacoustic emissions were evaluated to further understand the effect of the (+) enantiomer on hearing loss. Using animals from the acoustic trauma study, otoacoustic emissions were evaluated following administration of 5, 10, or 20 mg/kg of the (+) enantiomer.

The (+) enantiomer (20 mg/kg) significantly reduced DPOAE amplitude loss from baseline to day 14 by a mean of 51.2%, suggesting significantly reduced loss of outer hair cells in the cochlea (FIG. 3).

Effect of Oral Administration of Racemic Azasetron

The ability of the racemic azasetron hydrochloride by oral administration to reduce SSNHL after acoustic trauma was also evaluated. 10 mg/kg of azasetron or vehicle control (physiological saline) were administered to rats by oral gavage immediately after acoustic trauma (same protocol as above), followed by daily dosing for a total of 14 days.

Figure 4:
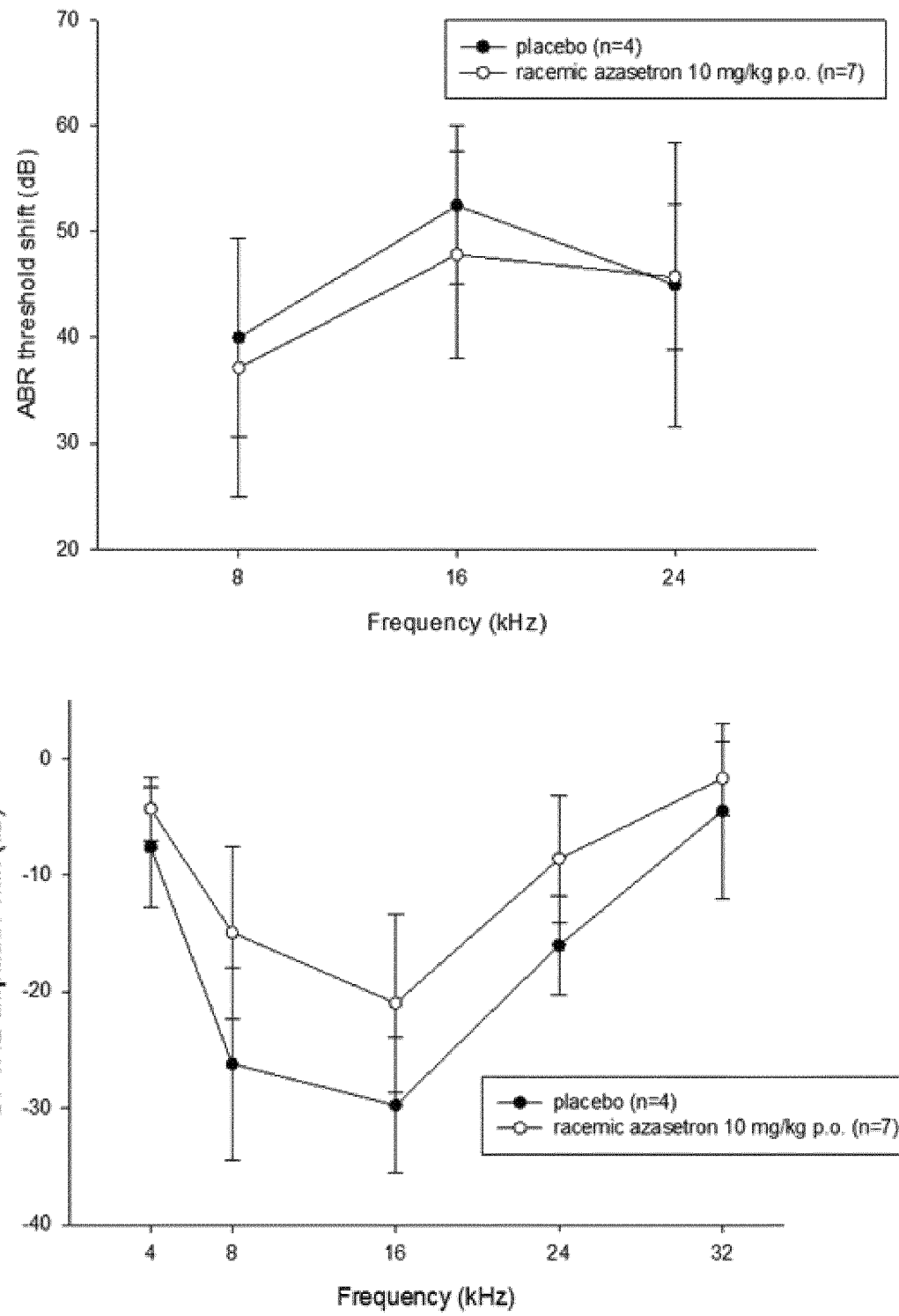
FIG. 4 is a set of two graphs showing the effect of azasetron racemate treatment against acoustic trauma by oral administration.

A small tendency towards a protective effect of the racemic azasetron hydrochloride was observed on ABR thresholds and DPOAE amplitude loss (FIG. 4), but unlike treatment with the same dose of (+)-azasetron (FIG. 3), it did not reach statistical significance.

Example 3: Activity of (+)-Azasetron Besylate on Cisplatin-Induced Hearing Loss and Ototoxicity The activity of (+)-azasetron besylate to protect against cisplatin ototoxicity induced hearing loss was evaluated by assessing effects on ABR threshold shift and DPOAE amplitude loss after slow intravenous cisplatin infusion in female Wistar rats (8 mg/kg cisplatin, 30-minute infusion). After baseline audiometry, rats were randomly assigned to receive daily placebo or (+)-azasetron besylate treatment for 14 days initiated 15 minutes before cisplatin administration. ABR threshold shifts and DPOAE amplitude loss were evaluated on day 14 (D14).

Figure 5:
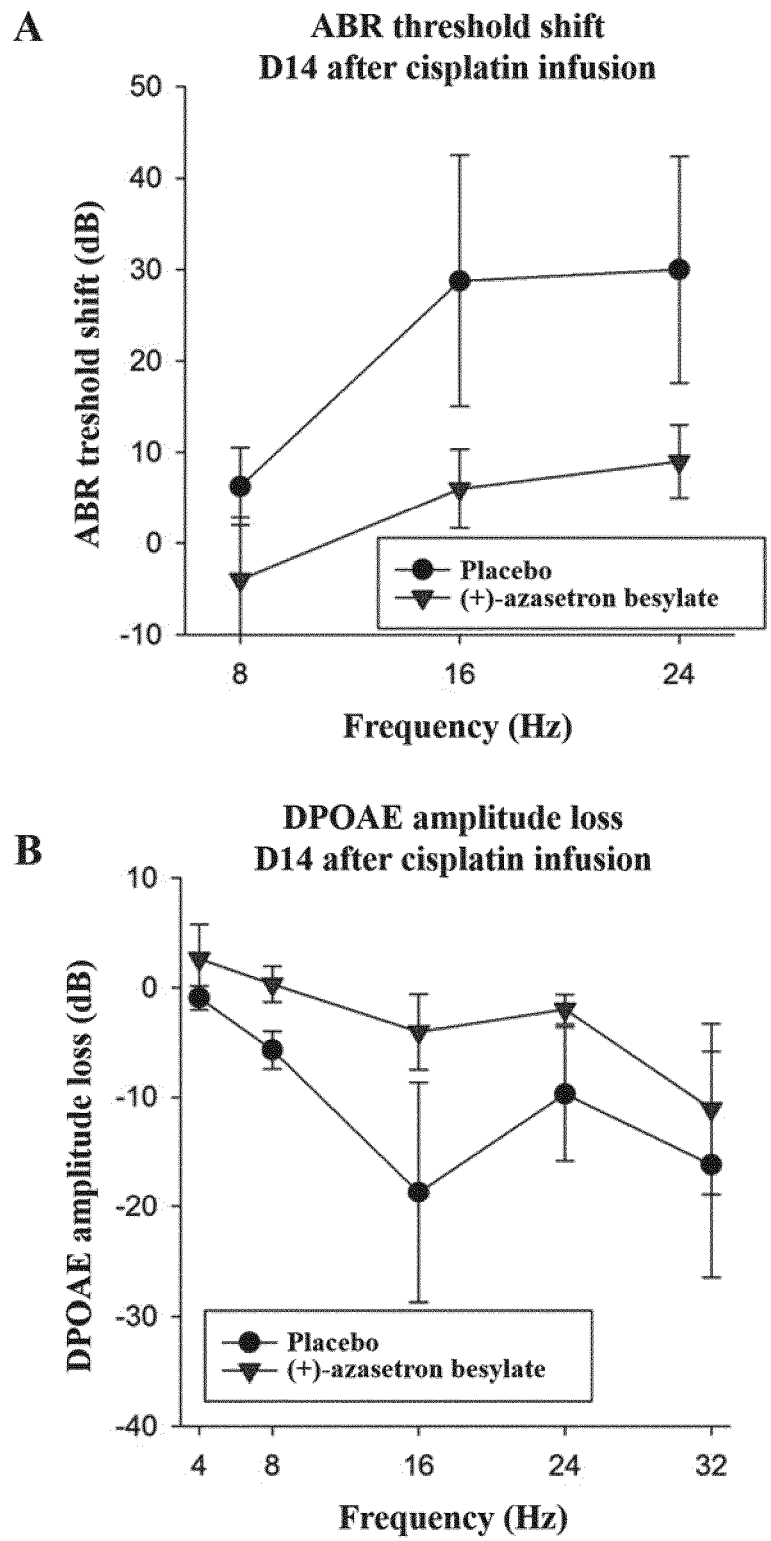
FIG. 5 is a set of two graphs showing auditory brainstem response (ABR) threshold shifts (A) and distortion product otoacoustic emission (DPOAE) amplitude loss (B) following cisplatin infusion after 14 days of oral treatment with placebo (n=4) or 26.4 mg/kg (+)-azasetron besylate (n=5).

In an initial study, animals were divided into 2 groups: Placebo (n=4) and 26.4 mg/kg (+)-azasetron besylate (corresponding to 18.2 mg/kg (+)-azasetron free-base, n=5), both administered by oral gavage for a total of 14 days. Two days after baseline audiometry (ABR and DPOAE measurements), oral treatment was initiated in both groups 15 minutes before 8 mg/kg cisplatin infusion during 30 minutes under isoflurane anesthesia. On D14, ABR and DPOAE measurements were performed to evaluate ABR threshold shifts and DPOAE amplitude loss relative to baseline and the temporal bones of each animal were subsequently preserved with PFA fixation for histology (FIG. 5).

Daily oral treatment with 26.4 mg/kg significantly reduced both ABR threshold shifts (~10-23 dB, up to 79% reduction) (FIG. 5A) and DPOAE amplitude loss (~3.5-15 dB, up to 78% reduction) (FIG. 5B) at D14 after cisplatin infusion compared to the placebo treated group.

Figure 7:
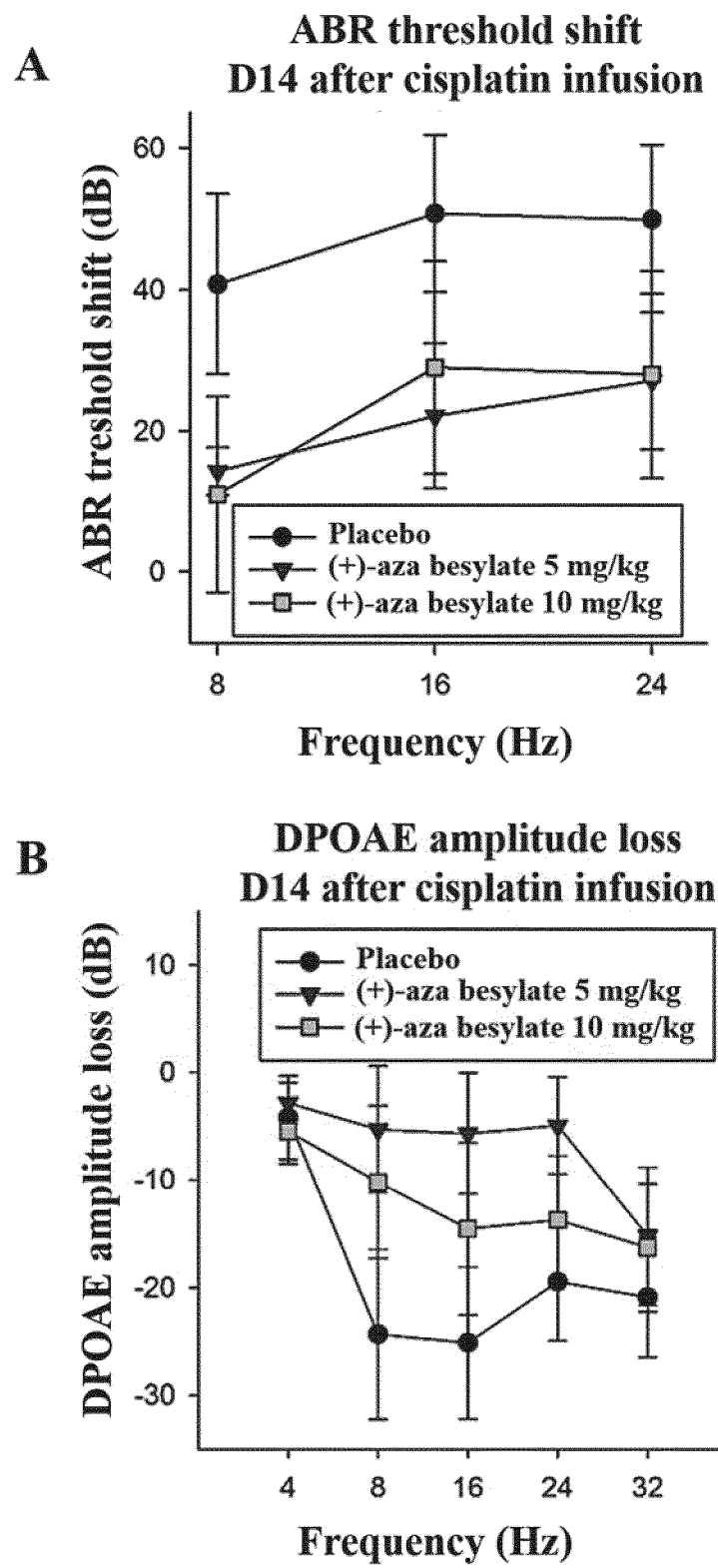
FIG. 7 is a set of two graphs showing auditory brainstem response (ABR) threshold shifts (A) and distortion product otoacoustic emission (DPOAE) amplitude loss (B) following cisplatin infusion after 14 days of oral treatment with placebo (n=6), 6.6 mg/kg (+)-azasetron besylate (n=7) or 13.2 mg/kg (+)-azasetron besylate (n=5).

In a follow-up study with lower doses of (+)-azasetron besylate, animals were divided into 3 groups: Placebo (n=6), 6.6 mg/kg (+)-azasetron besylate (corresponding to 5 mg/kg (+)-azasetron free-base, n=7) and 13.2 mg/kg (+)-azasetron besylate (corresponding to 10 mg/kg (+)-azasetron free-base, n=5), both administered by oral gavage for a total of 14 days. Two days after baseline audiometry (ABR and DPOAE measurements), oral treatment was initiated in both groups 15 minutes before 8 mg/kg cisplatin infusion for 30 minutes under isoflurane anaesthesia. On D14, ABR and DPOAE measurements were performed to evaluate ABR threshold shifts and DPOAE amplitude loss relative to baseline (FIG. 7).

Both 6.6 mg/kg (+)-azasetron besylate (~23-29 dB, up to 65% reduction) and 13.2 mg/kg (+)-azasetron besylate (22-29 dB, up to 73% reduction) daily oral treatment significantly reduced ABR threshold shifts compared to placebo (FIG. 7A) and the reduction of DPOAE amplitude loss by 6.6 mg/kg (+)-azasetron besylate (1.5-19 dB, up to 78% reduction) also reached statistical significance (FIG. 7B).

Figure 6:
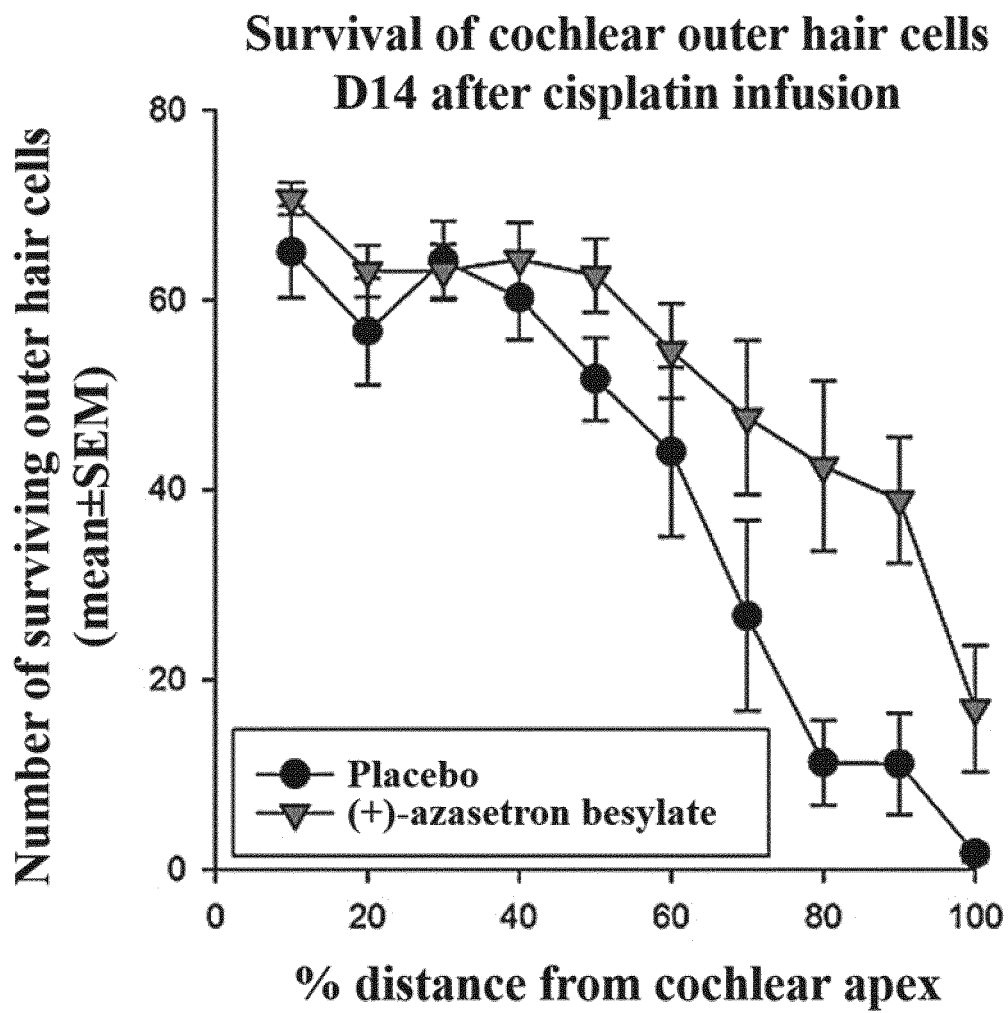
FIG. 6 is a graph showing the survival of cochlear outer hair cells following cisplatin infusion after 14 days of oral treatment with placebo (n=4) or 26.4 mg/kg (+)-azasetron besylate (n=5).
Figure 8:
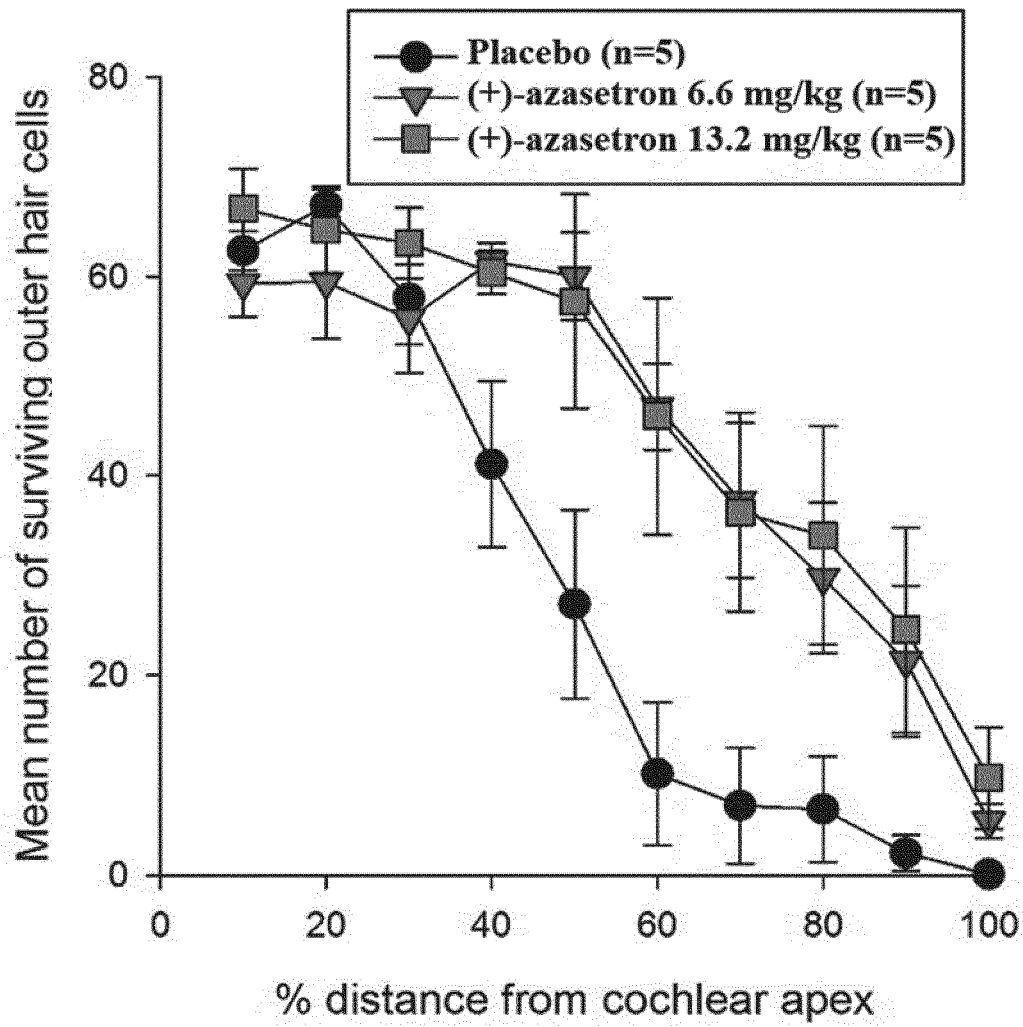
FIG. 8 is a graph showing the survival of cochlear outer hair cells following cisplatin infusion after 14 days of oral treatment with placebo (n=5), 6.6 mg/kg (n=5) or 13.2 mg/kg (n=5) (+)-azasetron besylate treatment.

To evaluate the effect of (+) azasetron on outer hair cells (OHC) survival after cisplatin administration at an ototoxic dose, cochleograms of surviving OHCs were constructed from whole-mount fixed *cochleae*. In placebo treated animals, 14 days after cisplatin administration the mean number of surviving OHCs per 200 μm segment had decreased significantly, starting at 40-60% distance from the apex and fell to ~10 cells or less in the basal turn. The number of surviving OHCs was significantly higher in animals having received 14 days of (+) azasetron treatment (p<0.001; FIGS. 6 and 8) and while hair cell loss was still observed, it was more gradual throughout the medial and basal turns, with conservation of up to 11-fold more OHCs in the basal turn of the cochlea, where the apoptotic effect was most prominent.

These data support the capacity of (+)-azasetron besylate to provide a significant benefit as a treatment against cisplatin induced ototoxicity, as demonstrated using functional audiometric measures of hearing (ABR threshold shift reduction, DPOAE amplitude loss reduction) corresponding to recognized clinical outcomes (pure tone audiograms, otoacoustic emissions) supported by histological demonstration of improved survival of cochlear outer sensory hair cells in cochleograms constructed from fixed tissue samples.

Example 4: Activity of (+)-Azasetron Besylate on Vestibular Dysfunction

The capacity of (+)-azasetron besylate to protect against lesions in the peripheral vestibular system was assessed using the kainate model of peripheral excitotoxic injury. Following unilateral, transtympanic injection of the excitotoxic kainic acid leading to the swelling, retraction and uncoupling of synapses between vestibular sensory hair cells and primary afferent neurons, baseline recordings of spontaneous nystagmus (pathological eye movements caused by a deficit of the vestibuloculomotor reflex) and postural deviations are performed before randomization to treatment groups. Recordings were repeated daily for 3 days, then again at D6 and D13 after lesion induction.

Figure 9:
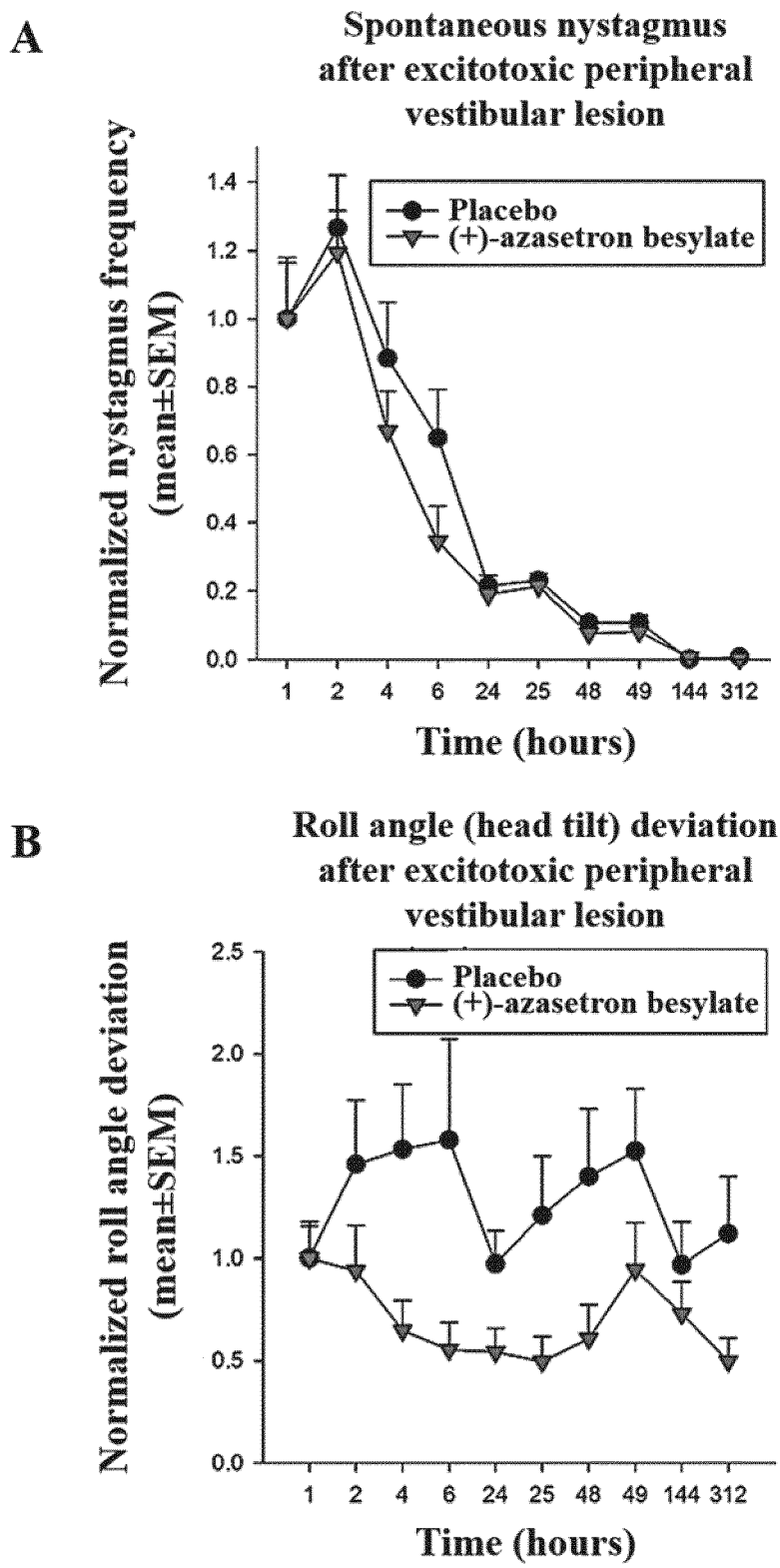
FIG. 9 is a set of two graphs showing the effect of (+)-azasetron besylate (5.6 mg/kg; n=16) versus placebo (n=18) on unilateral vestibular dysfunction induced by intratympanic kainic injection over time (in hours). A, Spontaneous nystagmus. B, Roll angle deviation.

Following lesion induction and baseline recordings at t=1h, female Long-Evans were randomized to receive intraperitoneal injections of placebo (n=18) or 5.6 mg/kg (+)-azasetron besylate daily for 3 days (t=1/24/25 h). Recording of spontaneous nystagmus and postural deviations were repeated at 2/4/6/24/25/48/49 hours and D6/D13 after initial lesion induction (FIG. 9).

(+)-azasetron besylate treatment significantly improved spontaneous nystagmus after excitotoxic peripheral vestibular lesion (p=0.048, 6-48% improvement), particularly in the early phase before central compensation of the vestibulooculomotor reflex deficits, already after the first administration. An early as well as lasting significant treatment effect of (+)-azasetron besylate administration (p<0.001, 30-62% improvement) was seen in the reduction of the roll angle deviation (postural head tilt) after excitotoxic peripheral vestibular lesion.

These data demonstrate the treatment benefit of (+)-azasetron besylate for reducing lesion induced deficits of the peripheral vestibular system of the inner ear.

The invention claimed is:

1. A method of treatment of a cochlear disease, disorder or condition in a patient afflicted with a cochlear disease, disorder or condition, wherein said method comprises the administration to the patient of a composition comprising
(+)-azasetron, of Formula (R)-I:

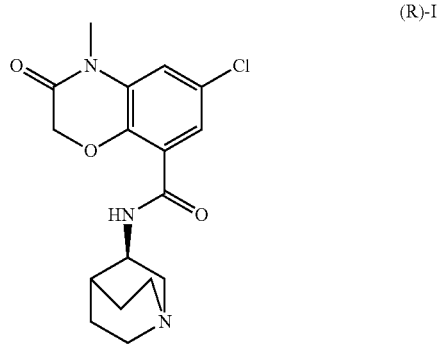 [SMILES: CN1C(=O)COc2c(C(=O)N[C@H]3CN4CCC3CC4)cc(Cl)cc21]

or a pharmaceutically acceptable salt and/or solvate thereof;
and at least one pharmaceutically acceptable excipient, wherein said cochlear disease, disorder or condition is sensorineural hearing loss or cochlear tinnitus.

2. The method according to claim 1, wherein the pharmaceutically acceptable salt is selected from the group consisting of: (+)-azasetron besylate, (+)-azasetron malate and (+)-azasetron hydrochloride.

3. The method according to claim 1, wherein the composition is administered at a dose of free-base (+)-azasetron, or a pharmaceutically acceptable salt and/or solvate thereof, ranging from about 0.01 mg/kg to about 100 mg/kg of body weight per day.

4. The method according to claim 1, wherein the composition is administered systemically or locally.

5. The method according to claim 4, wherein the composition is administered directly in the ear.

6. The method according to claim 5, wherein the composition is loaded on a device to be inserted into the cochlear duct or any other part of the cochlea.

7. The method according to claim 1, wherein the composition is administered orally.

8. The method according to claim 1, wherein said sensorineural hearing loss is ototoxic compound-induced sensorineural hearing loss.

9. The method according to claim 1, wherein said sensorineural hearing loss is platinum-induced sensorineural hearing loss.

10. The method according to claim 1, wherein said sensorineural hearing loss is cisplatin-induced sensorineural hearing loss.

11. The method according to claim 1, wherein the patient is diagnosed with cancer.

12. The method according to claim 1, wherein the patient is diagnosed with cancer and is receiving platinum-based chemotherapy.

13. The method according to claim 1, wherein the patient is diagnosed with cancer and is receiving cisplatin, carboplatin, oxaliplatin or a combination thereof.

14. The method according to claim 1, wherein the patient is diagnosed with cancer and wherein the composition is administered during and/or after platinum-based chemotherapy.

15. The method according to claim 1, wherein the patient is diagnosed with cancer and wherein the composition is administered during and/or after cisplatin-, carboplatin- or oxaliplatin-based chemotherapy or a combination thereof.

16. The method according to claim 1, wherein said sensorineural hearing loss is sudden sensorineural hearing loss or noise-induced sensorineural hearing loss.

17. The method according to claim 16, wherein said sudden sensorineural hearing loss is idiopathic sudden sensorineural hearing loss.

18. The method according to claim 1, wherein the composition is an immediate release composition or a sustained release composition.

19. The method according to claim 1, wherein the composition is an orodispersible composition.

20. The method according to claim 1, wherein the composition comprises at least a 90:10 w/w mixture of (+)-azasetron of Formula (R)-I:(−)-azasetron.

* * * * *